United States Patent
Conti et al.

[11] Patent Number: 5,919,811
[45] Date of Patent: Jul. 6, 1999

[54] 3-SUBSTITUTED-INDOLE-2-CARBOXYLIC ACID DERIVATIVES AS EXCITATORY AMINO ACID ANTAGONISTS

[75] Inventors: Nadia Conti; Romano Di Fabio; Elisabetta De Magistris; Aldo Feriani, all of Verona, Italy

[73] Assignee: Glaxo Wellcome S.p.A., Verona, Italy

[21] Appl. No.: 08/894,702

[22] PCT Filed: Mar. 1, 1996

[86] PCT No.: PCT/EP96/00840

§ 371 Date: Sep. 9, 1997

§ 102(e) Date: Sep. 9, 1997

[87] PCT Pub. No.: WO96/27588

PCT Pub. Date: Sep. 12, 1996

[30] Foreign Application Priority Data

Mar. 4, 1995 [GB] United Kingdom ............ 9504361

[51] Int. Cl.[6] ............ C07D 209/42; C07D 405/12; C07D 401/12; A61K 31/40
[52] U.S. Cl. ............ 514/419; 548/467; 548/492
[58] Field of Search .................... 548/492, 467; 514/419

[56] References Cited

U.S. PATENT DOCUMENTS

| | | | |
|---|---|---|---|
| 5,145,845 | 9/1992 | Johnson et al. ............ | 514/80 |
| 5,373,018 | 12/1994 | Cugola et al. ............ | 514/419 |
| 5,374,648 | 12/1994 | Cugola et al. ............ | 514/419 |
| 5,374,649 | 12/1994 | Cugola et al. ............ | 514/719 |
| 5,519,048 | 5/1996 | Salituro et al. ............ | 514/419 |

FOREIGN PATENT DOCUMENTS

| | | |
|---|---|---|
| 2266091 | 10/1993 | United Kingdom . |
| 94 20465 | 9/1994 | WIPO . |

*Primary Examiner*—Mukund J. Shah
*Assistant Examiner*—Bruck Kifle
*Attorney, Agent, or Firm*—Bacon & Thomas, PLLC

[57] ABSTRACT

1. Compounds of formula (I)

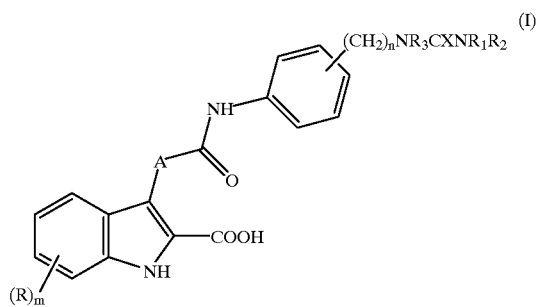

or a salt, or metabolically labile ester thereof, processes for their preparation, their use in medicine and intermediates for use in their preparation.

18 Claims, No Drawings

3-SUBSTITUTED-INDOLE-2-CARBOXYLIC ACID DERIVATIVES AS EXCITATORY AMINO ACID ANTAGONISTS

This invention relates to novel indole derivatives, to processes for their preparation, to pharmaceutical compositions containing them and to their use in medicine. In particular, it relates to indole derivatives which are potent and specific antagonists of excitatory amino acids.

WO92/16205 describes 3-substituted 2-carboxyindole derivatives which are useful in the treatment of neurodegenerative diseases. WO92/21153 also describes novel 3-substituted 2-carboxyindole derivatives which are potent antagonists at the strychnine insensitive glycine binding site located on the N-methyl-D-aspartate (NMDA) receptor complex and hence useful in the treatment of neurodegeneative diseases.

We have now found a further novel group of 3-substituted 2-carboxyindole derivative that have a specific antagonist activity at the strychnine insensitive glycine binding site located upon the NMDA receptor complex coupled with an advantageous pharmacological profile of activity.

Accordingly the present invention provides a compound of formula (I)

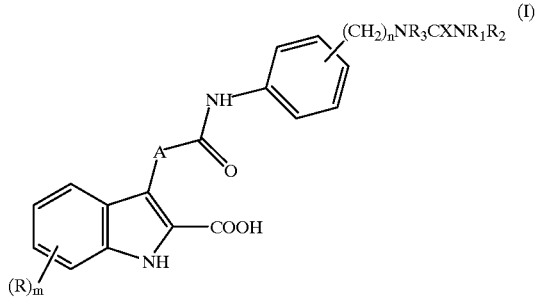

or a salt, or metabolically labile ester thereof wherein R represents a group selected from halogen, alkyl, alkoxy, amino, alkylamino, dialkylamino, hydroxy, trifluoromethyl, trifluoromethoxy, nitro, cyano, $SO_2R_4$ or $COR_4$ wherein $R_4$ represents hydroxy, methoxy, amino, alkylamino or dialkylamino; m is zero or an integer 1 or 2;

A represents an ethynyl or optionally substituted ethenyl group;

$R_1$ represents hydrogen or an optionally substituted alkyl, cycloalkyl, aryl or heterocyclic group;

$R_2$ represents hydrogen or alkyl; or $R_1$ and $R_2$ together with the nitrogen atom to which they are attached represent a 5–7 membered heterocyclic ring which may contain an additional heteroatom selected from oxygen sulphur or nitrogen;

$R_3$ represents hydrogen or alkyl;

n is zero or an integer from 1 to 4

X=O or S.

The compounds represented by formula (I) can exist in more than one isomeric form and all possible isomers are included in formula (I). Thus when the group A in the compound of formula (I) is an optionally substituted ethenyl group there can exist cis(Z) and (E) trans isomers and the invention includes all such isomers and a mixture thereof.

For use in medicine the salts of the compounds of formula (I) will be physiologically acceptable thereof. Other salts however may be useful in the preparation of the compounds of formula (I) or physiologically acceptable salts thereof. Therefore, unless otherwise stated, references to salts include both physiologically acceptable salts and non-physiologically acceptable salts of compounds of formula (I).

Suitable physiologically acceptable salts of compounds of the invention include base addition salts and where appropriate acid addition salts. Suitable physiologically acceptable base addition salts of compounds of formula (I) include alkali metal or alkaline metal salts such as sodium, potassium, calcium, and magnesium, and ammonium salts, formed with amino acids (e.g. lysine and arginine) and organic bases (e.g. procaine, phenylbenzylamine, ethanolamine diethanolamine and N-methyl glucosamine).

The compounds of formula (I) and/or salts thereof may form solvates (e.g. hydrates) and the invention includes all such solvates.

It will be appreciated that the compound of formula (I) may be produced in vivo by metabolism of a suitable prodrug. Such prodrugs include for example physiologically acceptable metabolically labile esters of compounds of the general formula (I). These may be formed by esterification, for example of any of the carboxylic acid groups in the parent compound of general formula (I) with where appropriate prior protection of any other reactive groups present in the molecule followed by deprotection if required. The types of ester grouping that may be used as metabolically labile esters are those widely used in pharmaceutical chemistry and are well known to those skilled in the art.

The term alkyl as used herein as a group or part of a group refers to a straight or branched chain alkyl group containing from 1 to 4 carbon atom examples of such groups including methyl, ethyl, propyl, isopropyl, n-butyl, isobutyl, secondary butyl or tertiary butyl.

The term substituted alkyl refers to alkyl substituted by one or more hydroxy, aminocarbonyl, carboxyl or amino groups.

The term optionally substituted ethenyl means an ethenyl group optionally substituted by 1 or 2 alkyl groups or an optionally substituted phenyl group and includes both cis and trans isomers. Example of such groups include ethenyl, 1-methylethenyl, 2-methylethenyl 1,2-dimethylethenyl or 1-phenylethenyl.

The term halogen refers to a fluorine, chlorine, bromine or iodine atom. The term cycloalkyl refers to a $C_{3-7}$ cycloalkyl group which may optionally be substituted or 1 or 2 $C_{1-4}$ alkyl groups e.g. cyclopropyl, cyclobutyl,cyclopentyl, cyclohexyl cycloheptyl or 2-methylcyclohexyl.

The term aryl refers to an optionally substituted phenyl group or a 5 or 6 membered heroaryl in which the 5-membered heteroaryl group contains 1 or 2 heteroatoms selected from oxygen sulphur or nitrogen and 6-membered heteroaryl group containing 1 or 2 nitrogen atoms. Example of suitable heteroaryl groups include furanyl, thiophenyl, imidazolyl, isoxazolyl, thiazolyl, oxazolyl, pyridyl, and pyrimidinyl.

The term optionally substituted phenyl refers to a phenyl group substituted with up to 3 substituents selected from halogen, $C_{1-4}$ alkyl, $C_{1-4}$ alkoxy, amino, alkylamino, dialkylamino, fluoro, chloro, hydroxy, trifluoromethyl, carboxyl or methoxycarbonyl.

The term optionally substituted heterocyclic group refers to 5–7 membered saturated heterocyclic group containing one or two heteroatoms selected from oxygen, sulphur or nitrogen. Examples of suitable groups containing a single heteroatom include tetrahydropyranyl e.g. 4-tetrahydropyranyl, pyrrolidinyl e.g. 2 or 3 pyrrolidinyl, piperidinyl. e.g. 4- or 3-piperidinyl and N-substituted derivative therefore (e.g. N-alkyl such as e.g. methyl or N-acyl such as N-alkanoyl e.g. acetyl or N-alkoxycarbonyl e.g. ethoxycarbonyl), piperidino or pyrrolidino. Examples of suitable groups containing 2 heteroatoms include morpholino, thiomophlino or piperazino.

When $R_1$ and $R_2$ together with the nitrogen atom to which they are attached represent an heterocyclic group, this refers to a 5–7 membered ring optionally containing an additional heteroatom selected from oxygen/sulphur or nitrogen and which ring is saturated or contains 1 or 2 double bonds. Example of suitable saturated groups include morpholino, 2,6 dimethylmorpholino, piperidino, pyrrolidino, piperazino or N-methylpiperazino. Examples of suitable heterocyclic groups containing 1 or 2 double bonds include N-imidazoline or N-imidazole.

In the compounds of formula (I) the group $(CH_2)nNR_3)R_1R_2$ may be at the 2, 3 or 4 position in the phenyl ring. Conveniently it is in the 3 or 4 position, and more preferably the 4 position.

In compounds of formula (I) the group X is conveniently oxygen.

A preferred class of compounds of formula (I) are those wherein m is 1 or 2 and within this class those wherein R is at the 4 and/or 6 position are particularly preferred. More preferably m is 2.

The group R is conveniently a halogen atom and preferably a chlorine atom.

When A is a substituted ethenyl group it is conveniently substituted by a single substituted at the 1-position. Examples of such groups include 1-methylethenyl and 1-phenylethenyl.

When A is an optionally substituted ethenyl group it is conveniently in the E configuration(trans isomer)

Most conveniently A is an unsubstituted ethenyl group in the E configuration.

Examples of suitable $R_1$ groups include hydrogen, alkyl e.g. methyl or ethyl, alkyl substituted by carboxyl e.g. carboxymethyl, cycloalkyl e.g. cyclopropyl or cyclohexyl, aryl e.g. phenyl (optionally substituted by for example methoxy) or pyridyl e.g. 3-pyridyl, or a heterocyclic group e.g. 4-tetrahydropyranyl.

Conveniently $R_2$ represents hydrogen or a methyl group.

The group $R_3$ is conveniently hydrogen.

A preferred group of compounds of formula (I) are those wherein $R_1$ represents or hydrogen, methyl, ethyl, carboxymethyl, phenyl optionally substituted by methoxy, cyclopropyl, cyclohexyl, 4-tetrahydropyranyl or 3-pyridyl, $R_2$ represents hydrogen or methyl and $R_3$ represents hydrogen. Within this group of compounds preferably $R_2$ and $R_3$ each represent hydrogen. Most preferably $R_1$; $R_2$ and $R_3$ each represent hydrogen.

Compounds of formula (I) wherein n is 2 or more particularly 1 represent a particularly preferred class of compounds according to the invention.

In compounds of formula (I) when n is zero conveniently X is oxygen, $R_1$ is hydrogen, methyl, phenyl, 3-pyridyl, or cyclohexyl, $R_2$ is hydrogen or methyl and $R_3$ is hydrogen, or more preferably $R_1$ $R_2$ and $R_3$ each represent hydrogen. Within this group of compounds those wherein the group $(CH_2)_n$ $NR_3CXNR_1R_2$ is in the 4 position, A is an unsubstituted ethenyl group in the tran configuration, m is 2 and R is chlorine in the 4 and 6 positions are especially preferred.

For the compounds of formula (I) wherein n is an integer from 1 to 4, conveniently $R_1$ is hydrogen, ethyl, phenyl optionally substituted by methoxy, carboxymethyl, cyclopropyl, 3-pyridyl or 4-tetrahydropyranyl and $R_2$ and $R_3$ are hydrogen. Within this class of compounds those wherein the group $(CH_2)_n$ $NR_3CXNR_1R_2$ is in the 3 or 4 position, n is 2 or more particularly 1, A is an unsubstituted ethenyl group in the trans configuration, m is 2 and R is chlorine in the 4 and 6 positions are preferred. A particularly preferred group of compounds from within this class of compounds are those wherein X is oxygen and more particularly $R_1$, $R_2$ and $R_3$ each represent hydrogen.

A particularly preferred compound according to the invention is 4,6-dichloro-3-[(E)-2'-(4'-ureidomethylphenylcarbamoyl)ethenyl]-1-H-indole-2-carboxylic acid and physiologically acceptable salts thereof.

Further preferred compounds of the invention include 4,6-dichloro-3-[(E)-2'-(4'-ethylureidomethylphenylcarbamoyl)ethenyl ]-1-H-indole-2-carboxylic acid;

4,6-dichloro-3-[(E)-2'-(4'-ethylthioureidomethylphenylcarbamoyl)ethenyl]-1-H-indole-2-carboxylic acid;

4,6-dichloro-3-[(E)-2'-(4'-phenylureidomethylphenylcarbamoyl)ethenyl ]-1-H-indole -2-carboxylic acid;

4,6-dichloro-3-[(E)-2'-(4'-ureidoethylphenylcarbamoyl)ethenyl]-1H-indole-2-carboxylic acid;

(E)4,6-dichloro-3-[2'-(4'-phenyl-ureido-phenylcarbamoyl)ethenyl]-1H-indole-2-carboxylic acid;

(E)-4,6-dichloro-3-[-2'-(4'-cyclopropyl-ureido-methyl-phenylcarbamoyl)-vinyl]-1H-indole-2-carboxylic acid;

(E)-4,6-dichloro-3-[2'-(3'-ureidomethyl)-phenylcarbamoyl)-ethrnyl]-1H-indole-2-carboxylic acid;

(E)-4,6-dichloro-3-{2'-[4'-(4"-methoxy-phenyl-ureidomethyl)-phenyl carbamoyl] ethenyl}-1H-indole-2carboxylic acid;

(E)-4,6-dichloro-3-[2'-(4'-tetrahydro-pyran-4"-yl-ureidomethyl)phenylcarbamoyl)-ethenyl]-1H-indole-2-carboxylic acid;

(E)4,6-dichloro-3-[2'-(4'-nicotin-3'-yl-ureido-methyl-phenylcarbamoyl)-ethenyl]-1H-indole-2-carboxylic acid;

(E)4,6-dichloro-3-[2'-(4'-carboxymethyl ureido-methyl-phenylcarbamoyl) ethenyl]-1H-indole-2-carboxylic acid;

4,6-dichloro-3-[(E)-2'-(4'-ureidophenylcarbamoyl)ethenyl]-1H-indole -2-carboxylic acid and physiologically acceptable salts thereof.

The compounds of formula (I) and or physiologically acceptable salts thereof are excitatory amino acid antagonists. More particularly they are potent antagonists at the strychnine insensitive glycine binding site associated with the NMDA receptor complex. As such they are potent antagonists of the NMDA. receptor complex. Moreover the compounds of the invention exhibit an advantageous profile of activity. These compounds are therefore useful in the treatment or prevention of neurotoxic damage or neurodegenerative diseases. Thus the compounds are useful for the treatment of neurotoxic injury which follows cerebral stroke, thromboembolic stroke, hemorrhagic stroke, cerebral ischemia, cerebral vasospam, hypoglycemia, anaesia, hypoxia, anoxia, perinatal asphyxia cardiac arrest. The compounds are useful in the treatment of chronic neurodegenerative diseases such as; Huntingdon's disease, Alzheimer's senile dementia, amyotrophic lateral sclerosis, Glutaric Acidaemia type, multi-infarct dementia, status epilecticus, contusive injuries (e.g. spinal cord injury and head injury), viral infection induced neurodengeration, (e.g. AIDS, encephalopaties), Down syndrome, epilepsy, schizophrenia, depression, anxiety, pain, migraine, neurogenic bladder, irritative bladder disturbances, drug dependency, including withdrawal symptoms from alcohol, cocaine, opiates, nicotine, benzodiazepine, and emesis.

The potent and selective action of the compound of the invention at the strychnine- insensitive glycine binding site present on the NMDA receptor complex may be readily determined using conventional test procedures. Thus the ability to bind at the strychnine insensitive glycine binding site was determined using the procedure of Kishimoto H et al. J Neurochem 1981, 37 1015–1024. The selectivity of the action of compounds of the invention for the strychnine insensitive glycine site was confirmed in studies at other ionotropic known excitatory amino acid receptors. Thus compound of the invention were found to show little or no affinity for the kainic acid (kainate) receptor, a-amino-3-hydroxy-5-methyl4-isoxazole-propionic acid (AMPA) receptor or at the NMDA binding site.

Compounds of the invention have also been found to inhibit NMDA induced convulsions in mice using the procedure Chiamulera: C et al. Psychopharmacology (1990) 102, 551–552.

The neuroprotective activity of compounds of the invention may also be demonstrated in the middle cerebral artery occulsion preparation in mice using the procedure described by Chiamulera et al European Journal of Pharmacology 216 1992 335–336.

In these in-vivo experiments, compounds of the invention exhibit surprisingly good activity when administered by the intravenous route.

The ability of the compounds to inhibit pain may be demonstrated in conventional analgesic screens such as those described by J. J. Bennett, J. K. Xie Pain, 1988, 41 87–107

The invention therefore provides for the use of a compound of formula (I) and or physiologically acceptable salt or metabolically labile ester thereof for use in therapy and in particular use as medicine for antagonising the effects of excitatory amino acids upon the NMDA receptor complex.

The invention also provides for the use of a compound of formula (I) and/or a physiologically acceptable salt or metabolically labile ester thereof for the manufacture of a medicament for antagonising the effects of excitatory amino acids upon the NMDA receptor complex.

According to a further aspect the invention also provides for a method for antagonising the effects of excitatory amino acids upon the NMDA receptor complex, comprising administering to a patient in need thereof an antagonistic amount of a compound of formula (I) and/or a physiologically acceptable salt or metabolically labile ester thereof.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated the route of administration and the age and the condition of the patient and will be ultimately at the discretion of the attendant physician. In general however doses employed for adult human treatment will typically be in the range of 2 to 800mg per day, dependent upon the route of administration. Thus for parenteral administration a daily dose will typically be in the range 20–100 mg preferably 60–80mg per day. For oral administration a daily dose will typically be within the range 200–800mg e.g.; 400–600mg per day.

The desired dose may conveniently be presented in a single dose or as divided doses administered at appropriate intervals, for example as two, three, four or more sub-doses per day.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt or metabilcially labile ester thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation, implant, or rectal administration. Parenteral administration is preferred.

Tablets and capsules for oral administration may contain conventional excipients such as binding agents, for example, syrup, accacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs; or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; solubilizers such as surfactants for example polysorbates or other agents such as cyclodextrins; and preservatives, for example, methyl or propyl p-hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as solubilising, stabilising and/or dispersing agents, tonicity adjusters and buffering agents or pH adjustors. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetrafluoroethane, carbon dioxide or other suitable propellant, such as dichlorodifluoromethane, trichlorofluoromethane, dichloro-tetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable carrier such as lactose or starch. The powder composition may be presented in unit dosage form in for example capsules or cartridges of e.g. gelatin, or blister packs from which the powder may be administered with the aid of an inhaler or insufflator.

The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

Compounds of general formula (I) and salts thereof may be prepared by the general methods outlined hereinafter. In the following description, the groups R, X, n, $R_1$, $R_2$, $R_3$ are as defined for the compounds of formula (I) unless otherwise stated.

Compounds of formula (I) in which A is an optionally substituted ethenyl group may be prepared from the compounds of formula (II) in which $R_1$, $R_3$, m and n have the meaning defined in formula (I), A is an optionally substituted ethenyl group, $R_5$ is carboxylic protecting group and $R_6$ represents hydrogen or a nitrogen protecting group

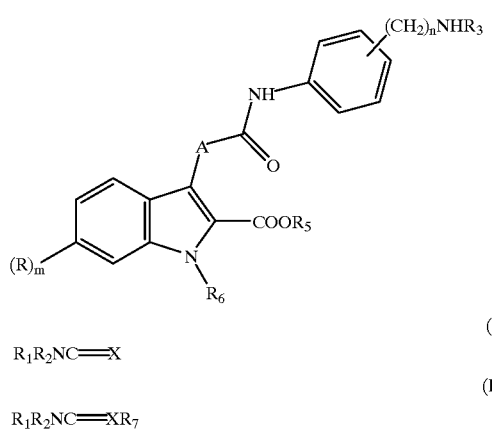

(II)

$R_1R_2NC\!\!=\!\!X$ (III)

$R_1R_2NC\!\!=\!\!XR_7$ (IV)

by reaction with the compounds of formula (III) wherein X represents oxygen or sulphur and $R_1R_2$ have the meanings defined in formula (I) or is protected derivatives thereof, or the compounds (IV) wherein the $R_1$ and $R_2$ have the. meaning defined in formula (I) or are protected derivatives thereof and $R_7$ is optionally substituted phenoxy, halogen, or imidazole group followed where necessary or by subsequent removal of the carboxyl protecting group $R_5$ and any nitrogen protecting group $R_6$ The reaction with the compound (III) is conveniently carried out in a solvent such as tetrahydrofuran or aqueous tetrahydrofuran, a halohydrocarbon (e.g. dichloromethane), or acetonitrile optionally in the the presence of a base such as triethylamine, and at a temperature with the range of 0–80° C.

The reaction with the compound (IV) is preferably carried out in a solvent such as a halohydrocarbon (e.g. dichloromethane) or an ether (e.g. tetrahydrofuran) or an amide (e.g. N,N-dimethylformamide) at a temperature with the range of room temperature to the reflux temperature of the solvent and optionally in the presence of a base such as a tertiary amine e.g. triethylamine. When the reaction is carried out using a compound of formula (IV) wherein $R_7$ is halogen the reaction is conveniently carried out at a temperature with the range 0–60° C.

Suitable carboxyl protecting groups $R_5$ for use in these reactions include allyl, alkyl, trichloroalkyl, trialkylsilylalkyl or arylmethyl groups such as benzyl, nitrobenzyl or trityl.

When $R_6$ is nitrogen protecting examples of suitable groups include alkoxycarbonyl e.g. t-butoxycarbonyl, arylsulphonyl e.g. phenysulphonyl or 2-trimethylsilylethoxymethyl.

In a further process of the invention compounds of formula (I), wherein R, m, $R_5$ and $R_6$ have the meanings defined above and A is optionally substituted ethenyl group may be prepared by reaction of an activated derivative of the carboxylic acid (V)

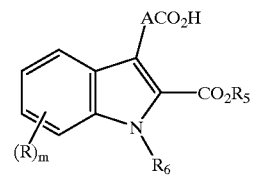

with the amine (VI)

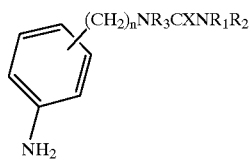

wherein $R_1$, $R_2$, $R_3$, n and X have the meanings defined in formula (I) or are protected derivative thereof followed where necessary by subsequent removal of the carboxyl protecting group $R_5$ and any nitrogen protecting group $R_6$.

Suitable activated derivatives of the carboxyl group include the corresponding acyl halide, mixed anhydride, activated ester such as a thioester or the derivative formed between the carboxylic acid group and a coupling agent such as that used in peptide chemistry, for example carbonyl diimidazole or a diimide such as dicyclohexylcarbodiimide.

The reaction is preferably carried out in an aprotic solvent such as a hydrocarbon, a halohydrocarbon, such as dichloromethane or an ether such as tetrahydrofuran.

Suitable carboxyl protecting groups $R_5$ for use in these reactions include allyl, alkyl, trichloroalkyl, trialkylsilylalkyl or arylmethyl groups such as benzyl, nitrobenzyl or trityl.

Suitable nitrogen protecting groups $R_6$ include alkoxycarbonyl e.g. t-butoxycarbonyl; arylsulphonyl e.g. phenysulphonyl or 2-trimethylsilylethoxymethyl.

The activated derivatives of the carboxylic acid (V) may be prepared by conventional means. A particularly suitable activated derivative for use in this reaction is thioester such as that derived from pyridine-2-thiol. These esters may conveniently be prepared by treating the carboxylic acid (V) with 2,2'-dithiopyridine and triphenylphosphine in a suitable aprotic solvent such as an ether e.g. tetrahydrofuran, a halohydrocarbon e.g. dichloromethane, an amide e.g. N,N-dimethylformamide or acetonitrile.

Compounds of formula (I) wherein A is optionally substituted ethenyl group may also be prepared from compounds of formula (VII) in which R and m have the means given above, $R_5$ is a carboxyl protecting group, $R_6$ is hydrogen or a nitrogen protecting group and $R_8$ is hydrogen atom or a $C_{1-4}$ alkyl group.

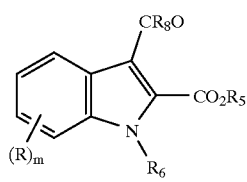

(VII)

by reaction with an appropriate phosphorus reagent capable of converting the group $CR_8O$ into the group

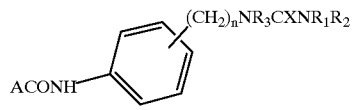

wherein n, X, $R_3$, $R_2$, $R_1$ have the meanings defined above for formula (I) followed where necessary or desired by removal of the carboxyl and/or nitrogen protecting group.

When $R_6$ is a nitrogen protecting example of suitable groups includes alkoxycarbonyl e.g. t-butoxycarbonyl or 2-trimethylsilylethoxymethyl or arylsulphonyl e.g. phenylsulphonyl.

Suitable carboxyl protecting groups include allyl, alkyl, trichloroalkyl, trialkylsilylalkyl or arylmethyl groups such as benzyl, nitrobenzyl or trityl.

In one embodiment of this process the reaction may be carried using a phosphorus ylide of formula (VIII)

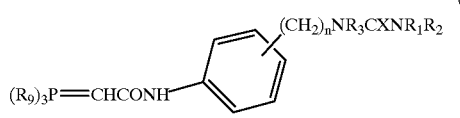

(VIII)

wherein $R_9$ is an alkyl or phenyl group, and $R_1$, $R_2$, $R_3$ X and n have the meanings defined above.

The reaction is carried out in aprotic solvent such as acetonitrile or an ether such as 1,4-dioxane and preferably with heating e.g. 40–120°. In a further embodiment of the process the reaction is carried out using a phosphonate of formula (IX)

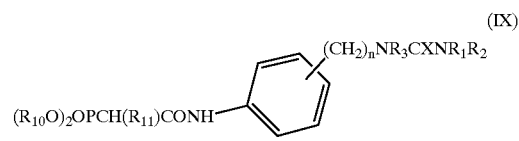

(IX)

wherein $R_{11}$ represents hydrogen, $C_{1-4}$ alky or optionally substituted phenyl; $R_{10}$ represents $C_{1-4}$ alkyl and $R_1$, $R_2$, $R_3$ have the meaning defined above.

The reaction is carried out in an aprotic solvent such as tetrahydrofuran and optionally with heating. Compounds of formula (I) wherein A is an ethynyl group may be prepared by reaction of the compound (X)

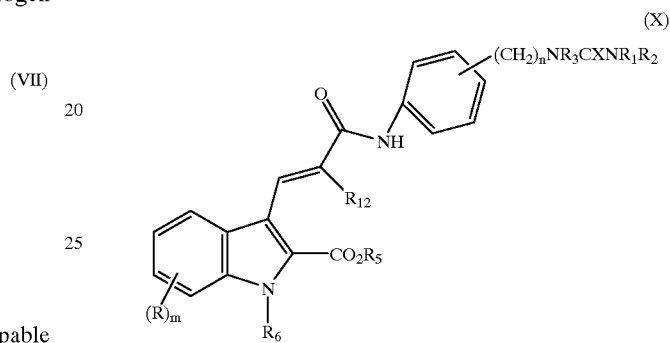

(X)

wherein $R_1$, $R_2$, $R_3$, m, n, and X have the meanings defined in formula (I) or are protected derivatives thereof, $R_5$ and $R_6$ have the meaning defined in formula (II) with the proviso that $R_6$ is not hydrogen and $R_{12}$ represents an halogen group such as chlorine, with a strong base lithium bis (trimethylsilyl)amide, followed by the removal of protecting groups $R_5$ and $R_6$.

The reaction is carried out in an protic solvent such as ether e.g. tetrahydrofuran and a temperature within the range –20 to +20° C. The protecting groups $R_5$ and $R_6$ may be removed by conventional procedures. Compounds of formula (I) wherein A is an unsubstituted ethenyl group with the cis configuration may be prepared from the corresponding compound of formula (I) wherein A is ethynyl or a protective derivative thereof by reduction using hydrogen and palladium or a calcium carbonate/lead oxide support as catalyst, followed where necessary by removal of any protecting group.

In any of the above reactions the carboxyl protecting group $R_5$ may be removed by conventional procedures known for removing such groups. Thus compounds when $R_5$ is an alkyl group, this may be removed by hydrolysis using an alkali metal hydroxide e.g. lithium hydroxide or sodium hydroxide in a solvent such as an alkanol e.g. ethanol or isopropanol, followed where desired or necessary by that addition of a suitable acid e.g. hydrochloric acid to give the corresponding free carboxylic acid.

In any of the above reactions the nitrogen protecting group may be removed by conventional procedures known for removing such groups, for example by acid or base hydrolysis. Thus when $R_6$ is alkoxycarbonyl e.g. t-butoxycarbonyl or phenylsulphonyl it may be removed by alkaline hydrolysis using for example sodium hydroxide or lithium hydroxide in a suitable solvent such as tetrahydrofuran or an alkanol e.g. isopropanol.

Physiologically acceptable salts of compounds of formula (I) may be prepared by treating the corresponding acid with an appropriate base in a suitable solvent. For example alkali and alkaline metal salts may be prepared from an alkali or alkaline metal hydroxide, or the corresponding carbonate or bicarbonate thereof. Alternatively alkali or alkaline metal salts may be prepared by direct hydrolysis of carboxyl protected derivative of compound of formula (I) with the appropriate alkali or alkaline metal hydroxide.

Metabolically labile esters of compounds of formula (I) may be prepared by esterification of the carboxylic acid group or a salt thereof or by trans esterfication using conventional procedures.

Compound of formula (II) may be prepared from an activated derivative of carboxylic acid (V) and amine (XI)

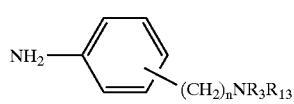

(XI)

wherein $R_3$ has the meaning defined in formula (I) and $R_{13}$ is nitrogen protecting group as defined above for $R_6$, using similar reaction conditions for those described above for the reaction compounds of formula (V) with compounds (VI) followed by the removal of the nitrogen protecting groups $R_{13}$. Compounds of formula (V) wherein A is an optionally substituted ethenyl group may be prepared from compound of formula (VII) and a phosphorus ylide $(R_9)_3P=CH\ CO_2Bu^t$ or phosphonate $(R_{10}O)_2OP—CH\ (R_{11})CO_2Bu^t$ using similar reaction conditions for those described above for the reaction of (VII) with the compounds of formula (VII) or (IX) followed by removal of the t-butyl protecting group.

The compounds of formula II wherein $R_1$, $R_3$ and m have the meanings defined in formula (I), A is an optionally substituted ethenyl group, n is 1 to 4, $R_5$ is hydrogen or a carboxyl protecting group and $R_6$ is hydrogen or a nitrogen protecting group are novel compounds and useful intermediates for the preparation of the corresponding compounds of formula (I).

Thus in a further aspect the invention provides compounds of formula (II) wherein $R_1$, $R_3$ and m have the meanings defined in formula (I), A is an optionally substitued ethenyl group, n is 1 to 4, $R_5$ is hydrogen or a carboxyl protecting group and $R_6$ is hydrogen or a nitrogen protecting group and salts thereof. Particularly useul compounds of formula (II) are those wherein A is an ethenyl group in the trans configuration, m is 2, R is chlorine in the 4 and 6 positions and $R_3$ is hydrogen, and more particularly n is 1 or 2. Conveniently the group $(CH_2)nNHR_3$ is at the 4 position in the phenyl ring.

The compounds of formula (II) wherein $R_5$ and $R_6$ are hydrogen are also potent and selective antagonists at the strychnine insensitive binding site on the NMDA receptor complex.

Compounds of formula (VII) are either known may be prepared according to the process described in EP No 568136 and WO 94/204605.

The compounds of formula (VIII) and (IX) are either known compounds or may be prepared by analogous methods to these described for the known compounds. The compounds of formula (V) or (VI) are either known or may be prepared using methods described for analogous compounds.

Compounds of formula (X) may be prepared from compounds of formula (VII) and a phoshonate (XII)

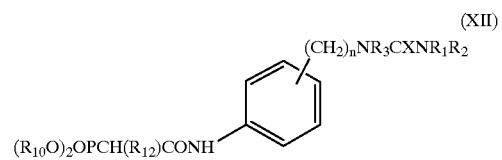

using similar reaction condition for those described above for the reaction of (VII) with the phosphonate (IX)

In order that the invention may be more fully understood the following examples are given by way of illustration only.

In the Intermediates and Examples unless otherwise stated:

Melting points (m.p.) were determined on a Gallenkamp m.p. apparatus and are uncorrected. All temperature refers to °C. lnfrared spectra were mesured on a FT-IR instrument. Proton Magnetic Resonance ($^1$H-NMR) spectra were recorded at 300 MHz, chemical shifts are reported in ppm downfield (d) from $Me_4Si$, used as internal standard, and are assigned as singlets (s), doublets (d), doublets of doublets (dd), triplets (t), quartets (q) or multiplets (m). Colum chromathography was carrier out over silica gel (Merck AG Darmstaadt, Germany). The following abbreviations are used in text: EA=ethyl acetate, CH=cyclohexane, DCM=dichloromethane. Tic refers to thin layer chromatography on silica plates. Solution were dried over anhydrous sodium sulphate. rt=room temperature

INTERMEDIATE 1

(E)4,6-dichloro-2-ethoxycarbonyl-3-(2'-tert-butoxycarbonylethenyl)-1-phenylsulfonyl-indole Sodium hydride (0:35 g) was dissolved in dry dimethylformamide (60 ml) and cooled at 0° then a solution of 4,6-dichloro-2ethoxycarbonyl-3-(E)-(2'-tert-butoxycarbonylethenyl)-1-H-indole (5.14 g) in dimethylformamide (40 ml) was added The reaction mixture was stirred for 45 min at 0° then phenylsulfonyl chloride (1.87 ml) was added and the solution stirred overnight at r.t. The solution was poured into a 0.5N aqueous solution of hydrochloric acid and extracted with ethyl acetate (400 ml). The organic phase was washed with a solution of sodium hydrogencarbonate and brine, then dried and evaporated obtaining the title compound as a yellow solid (6.64 g) $R_f$=0.78 (ethylacetate/cyclohexane=1/2 as eluant).

$^1$H-NMR ($CDCl_3$): 8.05 (1H; d); 8.01 (2H, d); 7.97 (1H, d); 7.63 (1H, t); 7.52 (2H, t); 7.28 (1H, d); 6.15 (1H, d); 4.51 (2H, m); 1.50 (9H, s); 1.43 (3H, t). IR (Nujol) ($cm^{-1}$): 1724 (C=O); 1711.

INTERMEDIATE 2

(E)4,6-dichloro-2-ethoxycarbonyl-3-(2'-carboxyethenyl)-1-phenylsulfonyl-indole

Intermediate 1 (6.6 g) was dissolved in formic acid (200 ml) and stirred for 3 hrs then evaporated affording the title compound (5.8 g)

$^1$H-NMR ($CDCl_3$): 8.05 (1H; d); 8.01 (2H, d); 7.97 (1H, d); 7.63 (1H, t); 7.52 (2H, t); 7.28 (1H, d); 6.15 (1H, d); 4.51 (2H, m); 1.50 (9H, s); 1.43 (3H, t).

INTERMEDIATE 3

(E)4,6-dichloro-2-ethoxycarbonyl-3-[-2'-(4'-N-tert-butoxycarbonylamino methylphenyl carbamoyl) ethenyl]-1-phenylsulfonyl-indole Intermediate 2 (5.14 g) was suspended in dry tetrahydrofuran (300 ml) and 2,2'-dipyridyl disulfide (3.36 g) and triphenylphosphine (4 g) were added. The reaction mixture was stirred for 2.5 hrs at r.t. until the mixture was a clear solution. Then 4-amino-N-tert-butoxycarbonyl-benzylamine (2.44 g) was added and the solution was refluxed for 3.5 hrs and overnight at r.t. The solvent was evaporated and the solid triturated with dichloromethane (100 ml) then filtered affording the title compound (4 g).

$^1$H-NMR (DMSO): 10.4 (bs, 1H); 8.09 (2H; d); 8.00 (1H, d); 7.95 (1H, d); 7:82 (1H, t); 7.70 (2H, t); 7.62 (2H, d); 7.65 (1H, d); 7.30 (1H, t); 7.18 (2H, d): 6.51 (1H, d); 4.48 (2H, q); 4.06 (2H, d); 1.40 (9H, s); 1.30 (3H, t).

INTERMEDIATE 4

(E)4,6-dichloro-2-ethoxycarbonyl-3-[2'-(4'-aminomethylphenyl carbamoyl)ethenyl]-1-phenylsulfonyl-indole Intermediate 3 (2.5 g) was suspended in dichloromethane (25 ml) and trifluoroacetic acid (10 ml) was added obtaining a solution, that stirred for 1.5 hrs at r.t. The sovent was evaporated and the solid was treated with at 10% solution of sodium hydrogencarbonate and extracted with ethylacetate. The organic layer was washed with brine, dried and evaporated affording the title compound (2.1 g).

$^1$H-NMR (DMSO): 10.34 (s, 1H); 8.07 (2H; d); 8.00 (1H, d); 7.93 (1H, d); 7.80 (1H, t); 7.69 (2H, t) 7.65 (1H, d); 7.63 (2H, d); 7.30 (2H, d); 6.49 (1H, d); 5.00 (2H, vvb); 4.47 (2H, q); 3.73 (2H, s); 1.31 (3H, t).

INTERMEDIATE 5

(E)4,6-dichloro-2-ethoxycarbonyl-3-[-2'-(4'-ureidomethyl phenylcarbamoyl)ethenyl]-1-phenylsulfonyl-indole Intermediate 4 (2.1 g) was dissolved in dry tetrahydrofuran (80 ml) and cooled at 0°. Trimethylsilylisocyanate (0.94 ml) was added and the reaction mixture was stirred at 10° for 3 hrs. A white solid precipitated. The reaction mixture was stirred overnight at r.t. then the precipitated was filtered and washed with diethylether obtaining the title compound (1.98 g)

$^1$H-NMR (DMSO): 10.36 (s, 1H); 8.07 (2H; d); 7.99 (1H, d); 7.93 (1H, d); 7.80 (1H, t); 7,69 (2H, t)7.64 (2H, d); 7.61 (2H, d); 7.19 (2H, d); 6.50 (1H, d); 6.37 (1H, t); 5.50 (2H, s); 4.47 (2H, q); 4.11 (2H, d); 1.40 (9H, s) 1.31 (3H, t).

INTERMEDIATE 6

(E)4,6-dichloro-2-ethoxycarbonyl-3-[2'-(4'-ethylureidomethylphenyl carbamoyl)ethenyl]-1-phenylsulfonyl-indole Intermediate 4 (0.250 g) was dissolved in dry tetrahydrofuran (2.6 ml). Ethylisocyanate (0.155 ml) was added and the reaction mixture was stirred at 40° C. for 3 hrs. A solid precipitates and the solvent was evaporated under vacuum then the solid obtained was triturated with diethylether and filtered, washing with diethyl ether obtaining the title compound (0.193 g; $R_f$=0.28 in ethylacetate/cyclohexane=2/1)

INTERMEDIATE 7

(E)4,6-dichloro-2-ethoxycarbonyl-3-[-2'-(4'-ethylthioureidomethyl phenylcarbamoyl)ethenyl]-1-phenylsulfonyl-indole Intermediate 4 (0.212 g) was dissolved in dry tetrahydrofuran (5 ml). ethylisothiocyanate (0.155 ml) was added and the reaction mixture was stirred at r.t. for 2 hrs. The solvent was evaporated under vacuum then the solid obtained was triturated with diethylether and filtered obtaining the crude compound which was purified by column chromathography (ethylacetate/cyclohexane=1/1) obtaining the title compound (0.125 g; $R_f$=057 in ethylacetate/cyclohexane=2/1)

$^1$H-NMR (DMSO): 10.35 (s, 1H); 8.07 (2H; d); 8.00 (1H, d); 7.94 (1H, d); 7.80 (1H, t); 7.69 (2H, t); 7.65 (1H, d); 7.62 (2H, d); 7.24 (2H, d); 7.8–7.4 (2H); 6.5 (1H, d); 4.59 (2H, ); 4.47 (2H, q); 3.37 (2H, q); 1.31 (3H, t); 1.08 (3H, t).

INTERMEDIATE 8

(E)4,6-dichloro-2-ethoxycarbonyl-3-[2'-(4'-N-tertbutoxycarbonylaminomethyl phenyl carbamoyl)ethenyl]-1HI-indole To a suspension of 4,6-dichloro-2-ethoxycarbonyl-3-(E)-(2'-carboxyethenyl)1-H-indole in dry tetrahydrofuran (250 ml) 2,2'-dipyridyl disulfide (2.77 g) and triphenylphosphine (3.3 g) were added. The reaction mixture was stirred for 3 hrs at r.t. until the mixture was a clear solution. Then 4-amino-N-tertbutoxycarbonyl-benzylamine (2.01 g) was added and the solution was refluxed for 3.5 hrs and overnight at r.t. The solvent was evaporated and the solid triturated with dichloromethane (80 ml) then filtered affording the title compound (4 g).

$^1$H-NMR (DMSO): 12.6 (1H, bs); 10.17 (1H, s); 8.23 (1H, d); 7.63 (2H, d); 7.50 (1H, d); 7.34 (1H, t); 7.31 (1H, d); 7.17 (2H, d); 6.75 (1H, d); 4.37 (2H, q); 4.06 (2H, d); 1.37 (9H, s); 1.34 (3H, t). IR (Nujol) (cm$^{-1}$): 3312–3125 (NH); 1717 (C=O); 1678 (C=O); 1640 (C=C).

INTERMEDIATE 9

4-N-tert-butoxycarbonylaminoethyl-phenylamine

Di-tert-butyl-dicarbonate (1.069 g) was added to a 0° cold solution of 2-(4-aminophenyl)-ethylamine (0.667 g) in ethylacetate (5 ml). The reaction mixture was stirred at r.t. for 4 hrs and a white solid precipitated. The solvent was evaporated under vacuum and the solid was triturated with petroleum ether, then filtered affording the title compound (1.09 g; $R_f$=0.9 in ethylacetate; m.p=52°).

INTERMEDIATE 10

(E)4,6-dichloro-3-[2'-(4'-tert-butoxycarbonylaminoethyl-phenylcarbamoyl)-ethenyl]-1-H-indole-carboxylic acid,ethylester 4,6-dichloro-2-ethoxycarbonyl-3-(E)-(2'-carboxyethenyl) 1-H-indole (0.5 g) was suspended in dry tetrahydrofuran (41 ml) and 2,2'-dipyridyl disulfide (0.46 g) and triphenylphosphine (0.55 g) were added. The reaction mixture was stirred for 3 hrs at r.t. until the mixture was a clear solution. Then intermediate 9 (0.39 g) was added and the solution was refluxed for 3.0 hrs. The solvent was evaporated and the solid was triturated with dichloromethane (20 ml) then filtered affording the title compound (0.5 g; $R_f$=0.6 in Ethylacetate/CH=1/1; m.p.=245° dec.).

INTERMEDIATE 11

(E)-3-[2'-(4'-tert-butoxycarbonyl-amino-phenylcarbamoyl)-ethenyl]-4,6-dichloro-1H-indole-2-carboxylic acid ethyl ester 2,2'-Dipyridyl disulfide (3.760 g) and triphenylphosphine (4.476 g) were added to a suspension of intermediate 2 (4 g)

in dry THF (100 ml) and the solution was stirred at r.t. for 2.5 h. 4-(tert-Butoxycarbonylamino)aniline (2.792 g) was then added and the reaction mixture was refluxed for 2 h. After cooling to r.t. the precipitate obtained was filtered giving the title compound (4.610 g) as a yellow solid.

$^1$H-NMR (DMSO): 12.58 (bs), 10.096 (bs), 9.27 (bs), 8.21 (d), 7.58 (d), 7.50 (d), 7.38 (d), 7.31 (d), 6.73 (d), 4.38 (q), 1.46 (s), 1.34 (t).

INTERMEDIATE 12

(E)-1-benzenesulphonyl-3-[2'-(4'-tert-butoxycarbonyl-amino-phenylcarbamoyl-ethenyl]-4,6-dichloro-1H-indole-2-carboxylic acid ethyl ester A solution of intermediate 11 (2.410 g) in dry DMF (30 ml) was added to a stirred suspension of sodium hydride (0.181 g; 80% suspension in mineral oil) in dry DMF (10 ml) at 0°. The reaction mixture was stirred at this temperature for 30 min then benzenesulfonyl chloride (0.770 ml) was added giving an orange suspension. The reaction mixture was stirred at r.t. for 3 h then was diluted with ethyl acetate (200 ml) and washed with water (4×150 ml). The organic extracts were dried and evaporated under reduced pressure to give the title compound (3.057 g) as a yellow solid.

$^1$H-NMR (CDCl3): 8.16 (d), 7.98 (d), 7.97 (d), 7.63 (t), 7.55 (t), 7.52 (d), 7.35 (d), 7.28 (d), 6.46 (sa), 6.38 (d), 4.48 (m), 1.5 (s), 1.38 (t).

INTERMEDIATE 13

(E)-3-[2'-(4'-amino-phenylcarbamoyl)-ethenyl]-1-benzenesulphonyl-4,6-dichloro-1H-indole-2-carboxylic acid ethyl ester Trifluoroacetic acid (13 ml) was added to a stirred suspension of intermediate 12 (3.368 g) in dichloromethane (40 ml) giving a dark red solution. The reaction mixture was stirred at r.t. for 1 h then the solvent was removed under reduced pressure. The oil obtained was repeatedly treated with diethyl ether and dried on the rotary evaporator to remove any residue of trifluoroacetic acid. Trituration with ethyl acetate and filtration of the solid obtained gave the title compound as a trifluoroacetate salt. This salt was dissolved in ethyl acetate (300 ml) and washed with NaHCO$_3$ (3×200 ml; 5%). The organic extracts were dried and evaporated under reduced pressure to give the title compound (1.993 g) as a yellow solid.

$^1$H-NMR (DMSO): 9.97 (bs), 8.06 (m), 7.99 (d), 7.85 (d), 7.79 (m), 7.68 (m), 7.63 (d), 7.33 (m), 6.50 (m), 6.44 (d), 4.94 (bs), 4.46 (q), 1.31 (t). IR (Nujol) (cm$^{-1}$): 3306 (N—H); 1722 (C=O).

INTERMEDIATE 14

(E)-1-benzenesulfonyl-4,6-dichloro-3-[2'-(4'-ureido-phenylcarbamoyl)-ethenyl]-1h-indole-2-carboxylic acid ethyl ester Intermediate 13 (0.100 g) was dissolved in dry THF (4 ml). Trimethylsilylisocyanate (0.034 ml; 85%) was added and the solution was stirred at r.t. for 3 h. An other amount of trimethylsilylisocyanate (0.034 ml; 85%) was added and the reaction mixture was stirred at 50° for 2 h. A white solid precipitated. The solvent was removed under reduced pressure. The residue was dissolved in diethyl ether/ethyl acetate and the solution washed with water. The organic extracts were dried and the solvent was removed under reduced pressure to give the title compound (0.101 g) as a solid.

$^1$H-NMR (DMSO): 10.23 (bs), 8.49 (bs), 8.07 (m), 8.00 (d), 7.90 (d), 7.81 (m), 7.69 and 7.65 (m and d), 7.53 (d), 7.34 (d), 6.47 (d), 5.81 (bs); 4.47 (q), 1.32 (t). IR (Nujol) (cm$^{-1}$): 3500–3200 (N—H); 1720, 1663 (C=O).

INTERMEDIATE 15

4-amino-benzyl-urea

Trimethylsilylisocyanate (3.2 ml; 85%) was added to a solution of 4-amino-benzylamine (1.55 ml) in dry THF (40 ml). A white solid precipitated. The reaction mixture was stirred at r.t. overnight then the precipitate was filtered and washed with ethyl acetate giving the title compound (1.2 g) as a white solid.

$^1$H-NMR (DMSO): 6.79 (d), 6.46 (d), 6.11 (t), 5.40 (s), 4.90 (s), 3.95 (d). IR (Nujol) (cm$^{-1}$): 3437, 3317 (N—H); 1641 (C=O).

INTERMEDIATE 16

(E)-1-benzenesulfonyl-4,6-dichloro-3-[-2'-(4'-phenyl-ureido-phenylcarbamoyl)-vinyl]-1H-indole-2-carboxylic acid ethyl ester Phenyl isocyanate (0.160 ml) was added to a solution of intermediate 13 (0.200 g) in dry THF (4 ml). The reaction mixture was refluxed for 10 min then cooled to r.t. The precipitated obtained was filtered giving the title compound (0.180 g) as a cream solid.

$^1$H-NMR (DMSO): 10.27 (bs), 8.68 (bs), 8.07 (d), 7.99 (d), 7.92 (d), 7.8 (m), 7.22 (m), 6.93 (m), 6.48 (d), 4.47 (q), 1.31 (t). IR (Nujol) (cm$^{-1}$): 3391, 3290 (N—H); 1734, 1661, 1651 (C=O).

INTERMEDIATE 17

(E)-1-benzenesulphonyl-4,6-dichloro-3-[2'-(4'-dimethyl-ureido-phenylcarbamoyl)-vinyl]-1H-indole-2-carboxylic acid ethyl ester Dimethylcarbamoyl chloride (0.040 ml) was added to a stirred solution of intermediate 13 (0.200 g) and triethylamine (0.050 ml) in dry THF (4 ml) at 0° C. The reaction mixture was refluxed for 8 h, cooled to r.t. then diluted with water (50 ml) and extracted with ethyl acetate (3×50 ml). The organic extracts were dried evaporated under reduced pressure. The residue was purified by flash chromatography using ethyl acetate as eluant to give the title compound (0.159 g) as a pale yellow solid.

$^1$H-NMR (DMSO): 10.23 (s), 8.24 (s), 8.07 (d), 8.00 (d), 7.91 (d), 7.80 (t), 7.69 (t), 7.65 (d), 7.53 (d), 7.40 (d), 6.48 (d), 4.47 (q), 2.9 (s), 1.32 (t). IR (Nujol) (cm$^{-1}$): 3298 (N—H); 1736, 1661, 1643 (C=O).

INTERMEDIATE 18

(E)-3-(2'-tert-butoxycarbonyl-ethenyl)-4,6-dichloro-1H-indole-2-carboxylic acid isopropyl ester Sodium hydride (1 g; 95%) was added in two 0.5 g portions to a solution of (tert-butoxycarbonylmethyl)-triphenylphosphonium bromide (8.4 g) in isopropanol (100 ml). After the evolution of hydrogen ceased ethyl-3-formyl-4,6-dichloro-indole-2-carboxylate (5 g) was added and the reaction mixture was refluxed for 2 h. (tert-Butoxycarbonylmethylene)-triphenylphosphorane (1 g) was added and the reflux was continued for 8 h. An other amount of (tert-butoxycarbonylmethylene)-triphenylphosphorane (3.5 g) was added and the reaction mixture was refluxed for additional 3 h. After cooling to r.t. the solution was poured into water and extracted with ethyl acetate. The organic extracts were dried and evaporated under reduced pressure. The residue was purified by flash chromatography using cyclohexane/ethyl acetate 3:1 as eluant to give the title compound (2.2 g) as a white solid.

$^1$H-NMR (CDCl$_3$): 9.2 (bs), 8.33 (d), 8.25 (d), 7.19 (d), 6.4 (d), 5.3 (m), 1.54 (s), 1.40 (d).

INTERMEDIATE 19

(E)-3-(2-carboxy-ethenyl-4,6-dichloro-4,6-1H-indole-2-carboxylic acid isopropyl ester A suspension of intermediate 18 (2.180 g) in formic acid (250 ml) was stirred at r.t. for 3 h then the acid was removed under reduced pressure to give the title compound (1.85 g) as an off white solid.

$^1$H-NMR (DMSO): 12.58 (bs), 12.37 (bs), 8.25 (d), 7.50 (d), 7.31 (d), 6.39 (d), 5.17 (m), 1.33 (d).

INTERMEDIATE 20

3-tert-butoxycarbonyl-aminomethyl-aniline

Iron powder (0.797 g) and calcium hydride dihydrate (0.105 g) were added to a solution of 3-tert butoxycarbonylaminomethyl nitrobenzene (0.400 g) in ethanol (8 ml; 95%). The reaction mixture was stirred at 70° C. for 4 h and refluxed for 2 h then allowed to cool to r.t. The iron powder was filtered and washed with ethyl acetate. The mother liquor was washed with water and the aqueous phase extracted with ethyl acetate. The organic extracts were dried and evaporated under reduced pressure. The residue was purified by flash chromatography using cyclohexane/ethyl acetate 1:1 as eluant to give the title compound (0.301 g) as a colorless oil.

$^1$H-NMR (CDCl$_3$): 7.11 (m), 6.72–6.55 (m), 4.78 (bm), 4.22 (d), 3.70 (bm), 1.46 (s).

INTERMEDIATE 21

(E)-3-[2'-(3'-tert-butoxycarbonyl-aminomethyl-phenylcarbamoyl)-ethenyl]-4,6-dichloro-1H-indole-2-carboxylic acid isopropyl ester 2,2'-Dipyridyl disulfide (0.334 g) and triphenylphosphine (0.398 g) were added to a solution of intermediate 19 (0.371 g) in dry THF (7 ml) and the reaction mixture was stirred at r.t. for 3 h. A solution of intermediate 20 (0.289 g) in dry THF (4 ml) was then added and the solution was refluxed for 1 h. The solvent was removed under reduced pressure and the residue was purified by flash chromatography using cyclohexane/ethyl acetate 65:35 as eluant followed by trituration with diethyl ether. Filtration of the solid obtained gave the title compound (0.300 g) as a white solid.

$^1$H-NMR (DMSO): 12.52 (bs), 10.17 (s), 8.23 (d), 7.60 (d), 7.58 (bs), 7.51 (d), 7.38 (t), 7.32 (d), 7.25 (t), 6.93 (d), 6.73 (d), 5.19 (m), 4.10 (d), 1.39 (s), 1.35 (d).

INTERMEDIATE 22

4,6-dichloro-2-ethoxycarbonyl-3-[(E)-2'-(4'-ethylureidophenylcarbamoyl) ethenyl]-1-phenylsulfonyl-indole To a solution of intermediate 13 (281 mg) in dry tetrahydrofuran (3 ml) ethyl isocyanate (0.179 ml) was added and the reaction mixture was stirred at 40° for 5 hrs. The solvent was then evaporated under vacuum and the solid obtained was triturated with diethylether and filtered, washing with diethyl ether obtaining the title compound (40.3 mg). m.p.>250°.

$^1$H-NMR (DMSO): 10.21 (1H, bs); 8.37 (1H; bs); 8.06 (2H, m), 7.99 (1H, d); 7.89 (1H, d); 7.80 (1H, m); 7.69 and 7.64 (3H, m and d); 7.52 (2H, m); 7.32 (2H, d); 6.47 (1H, d); 6.05 (1H, bt), 4.47 (2H, q); 3.07 (2H, m), 1.31 (3H, t), 1.02 (3H, t).

INTERMEDIATE 23

4,6-dichloro-2-ethoxycarbonyl-3-[(E)-2'-(4'-cyclohexylureidophenylcarbamoyl)ethenyl]-1-phenylsulfonyl-indole To a solution of intermediate 13 (207 mg) in dry tetrahydrofuran (3 ml). cyclohexyl isocyanate (0.213 ml) was added and the -reaction mixture refluxed at 80° for 4 hrs and at r.t. for 48 hrs. A solid precipitated and the solvent was evaporated under vacuum. Then the solid obtained was triturated with ethylacetate and filtered to obtain the title compound (40.3 mg). m.p.>250°.

$^1$H-NMR:(DMSO): 10.21 (1H, bs); 8.26 (1H, bs), 8.07 (2H, d), 7.99 (1H, d); 7.90 (1H, d); 7.80 (1H, t); 7.69 (2H, t), 7.65 (1H, d); 7.52 (2H, d); 7.31 (2H, d); 6.47 (1H, d); 6.04 (1H, bd), 4.47 (2H, q); 3.4 (1H, m), 1.8–1.2 (10H, m), 1.3 (3H, t).

INTERMEDIATE 24

4,6-dichloro-2-ethoxycarbonyl-3-[(E)-2'-(4'-cyclopropylureidophenylcarbamoyl)ethenyl]-1-phenylsulfonyl-indole To a solution of cyclopropane carboxylic acid (0.144 mg) in dry toluene (5 ml), TEA (0.253 ml) and diphenylphosphorylazide (0.392 ml) were added and the reaction mixture was stirred at r.t. for 3 hrs. The reaction was quenched with water and extracted with ethylacetate. The organic layer was dried and the solvent removed. The residue was dissolved in toluene (3 ml) and stirred at 80° for 1 h. The formation of the cyclopropyl isocyanate was followed by IR and the resulting solution was added to a solution of intermediate 13 (254 mg) in dry tetrahydrofuran (4 ml), and the reaction mixture stirred at 100° for 5 hrs. The precipitated solid was filtered and washed with ethylacetate to obtain the title compound (134 mg). m.p.>250°.

$^1$H-NMR (DMSO): 10.24 (1H, s); 8.25 (1H; s); 8.09 (2H, d), 8.01 (1H, d); 7.93 (1H, d); 7.82 (1H, tt); 7.71 (2H, t), 7.66 (1H, d); 7.56 (2H, d); 7.36 (2H, d); 6.50 (1H, d); 6.35 (1H, bd), 4.49 (2H, q); 2.54 (1H, m), 1.34 (3H, t), 0.53 (2H, m), 0.42 (2H, m).

INTERMEDIATE 25

4,6-dichloro-2-ethoxycarbonyl-3-[(E)-2'-(4'-nicotinylureidophenylcarbamoyl)ethenyl]-1-phenylsulfonyl-indole To a solution of nicotinic acid (224 mg) in dry toluene (5 ml), TEA (0.253 ml) and diphenylphosphorylazide (0.392 ml) were added and the reaction mixture was stirred at r.t. for 1 h. The reaction was quenched with water and extracted with ethylacetate. The organic layer was dried and the solvent removed. The residue dissolved in toluene (6 ml) was stirred at 80° C. for 2 h. The formation of the nicotinyl isocyanate was followed by IR. The solution is used as such for the next reaction.

To a solution of intermediate 13 (210 mg) in dry tetrahydrofuran (4 ml), a solution of intermediate nicotinyl isocyanate readily prepared was added and the reaction mixture stirred at 60° for 4 hrs and at r.t. overnight. The solid precipitated was filtered and washed with ethylacetate to obtain the title compound (190 mg).

$^1$H-NMR (DMSO): 10.30 (1H, bs); 8.99 (1H; bs); 8.77 (1H, bs), 8.59 (1H, m); 8.17 (1H, m), 8.07 (2H, m), 7.99 (1H, d); 7.91 (2H, d+m); 7.80 (1H, m), 7.69–7.64–7.61 (5H, m–d–d); 7.41 (2H, d); 7.30 (1H, m); 6.48 (1H, d), 4.47 (2H, q), 1.32 (3H, t).

INTERMEDIATE 26

4,6-dichloro-2-ethoxycarbonyl-3-[(E)-2'-(4'-(-tetrahydropyran-4"-yl)-ureidophenylcarbamoyl) ethenyl]-1-phenylsulfonyl-indole To a solution of tetrahydropyran-4-carboxylic acid (180 mg) in dry toluene (5.4 ml) triethylamine (0.192 ml) and diphenylphosphorylazide (0.297 ml) were added and the reaction mixture was stirred at r.t. for 1.5 hrs. The reaction was quenched with water and extracted with ethylacetate. The organic layer was dried with Na2SO4 and the solvent removed. The residue was then dissolved in toluene (4 ml) and stirred at 80° for 1 hr. The formation of the tetrahydropyran-4-yl isocyanate is followed by IR. The solution was used as such for the next reaction.

To a solution of intermediate 13 (254 mg) in dry tetrahydrofuran (4 ml), the solution of intermediate tetrahydropyran-4-yl isocyanate readily prepared was added and the reaction mixture stirred at 60° for 4 hrs. The solid precipitated, was filtered and washed with ethylacetate to obtain the title compound (166 mg). m.p.>250°.

$^1$H-NMR (DMSO): 10.22 (1H, bs); 8.33 (1H; bs); 8.07 (2H, d), 8.00 (1H, d); 7.89 (1H, d); 7.80 (1H, t); 7.69 (2H, t), 7.65 (1H, d); 7.54 (2H, d); 7.32 (2H, d); 6.47 (1H, d); 6.19 (1H, bd), 4.47 (2H, m); 3.80 (2H, m), 3.64 (1H, m), 3.4 (2H, m), 1.8–1.3 (4H, m), 1.3 (3H, t).

EXAMPLE 1

(E)4,6-dichloro-2-ethoxycarbonyl-3-[-2'-(4'-aminomethylphenylcarbamoyl)ethenyl]-1-H-indole To a suspension of intermediate 8 (0.6 g) in dichloromethane (6.8 ml), trifluoroacetic acid (2.9 ml) was added and stirred for 1.5 hrs at r.t. The sovent was evaporated and the solid was treated with a 10% solution of sodium hydrogencarbonate and extracted with ethylacetate (500 ml). The organic layer was washed with brine, dried and evaporated affording the title compound (0.4 g).

$^1$H-NMR (DMSO): 10.02 (1H, bs); 8.32 (1H, d); 7.63 (2H, d); 7.44 (1H, d); 7.24 (2H, d); 7.19 (1H, d); 6.69 (1H, d); 4.33 (2H, q); 3.65 (2H, s); 1.32 (3H, t). IR (Nujol) (cm$^{-1}$): 3425–3337 (NH, NH$_2$); 1704–1664 (C=O); 1607 (C=C).

EXAMPLE 2

(E)4,6-dichloro-3-[-2'-(4'-aminomethylphenylcarbamoyl)ethenyl]-1-H-indole-2-carboxylic acid, hydrochloride A solution of example 1 (0.102 g) in a 4/1 mixture of ethanol and water (5 ml) was treated with LiOH*H2O (0.025 g) for 3 hours at 60°. The solvent was then evaporated and the solid so obtained was triturated with 3N HCl for 1 hour. The suspension was then filtered and triturated with ether (5 ml) to give the title compound (0.06 g) as a yellow solid.

$^1$H-NMR (DMSO): 13.75 (s, 1H), 12.58 (s, 1H), 10.34 (s, 1H), 8.28 (d, 1H), 8.17 (s, 3H), 7.75 (d, 2H), 7.49 (d, 1H), 7.41 (d, 2H), 7.30 (d, 1H), 6.80 (d, 1H), 3.96 (m, 2H); IR (Nujol) (cm$^{-1}$): 3500–2400, 1650, 1610 m.p.>200°

EXAMPLE 3

(E)4,6-dichloro-3-[-2'-(4'-aminomethylphenylcarbamoyl)ethenyl]-1-H-indole-2-carboxylic acid Example 2 (0.029 g) was suspended in water and treated with 0.1N NaOH with stirring for 1 hour. The suspension was then lyophilized for 24 hours to give the title compound (0.031 g) as a yellow solid.

$^1$H-NMR (DMSO): 12.20 (s, 1H), 10.19 (s, 1H), 8.57 (d, 1H), 8.31 (s), 7.79 (d, 2H), 7.45 (d, 1H), 7.40 (d, 2H), 7.15 (d, 1H), 7.14 (d, 1H), 3.96 (s, 2H); IR (Nujol) (cm$^{-1}$): 3402, 3308, 1612

EXAMPLE 4

(E)4,6-dichloro-3-[2'-(4'-trifluoroacetateammonium-ethyl-phenylcarbamoyl)ethenyl]-1H-indole-carboxylic acid, ethylester Intermediate 10 (0.5 g) was suspended in dichloromethane (6.5 ml) and trifluoroacetic acid (2.5 ml) was added the yellow solution obtained was stirred for 1 hrs at r.t. The solvent was evaporated under vacuum and the solid obtained was triturated with ethylacetate and filtered to give the title compound (0.520 g) as a yellowsolid (m.p.=250° dec.).

$^1$H-NMR (DMSO): 12.61 (1H, s); 10.2 (s, 1H); 8.24 (1H; d); 7.73 (3H, bt); 7.67 (2H, t); 7.51 (1H, d); 7.32 (1H, d); 7.20 (2H, d); 6.77 (1H, d); 4.37 (2H, vvb); 3.02 (2H, m); 2.80 (2H, t); 1.34 (3H, t).

EXAMPLE 5

(E)4,6-dichloro-3-[2'-(4'-aminoethylphenylcarbamoyl)ethenyl]-1H-indole-carboxylic acid, ethylester Example 4 (0.32 g) was treated with a 0.5N solution of sodium hydroxide and the sospension was stirred for 10 min at r.t. The solid was filtered and washed with water affording the title compound (0.25 g).

$^1$H-NMR (DMSO): 10.13 (1H, s); 8.28 (1H, d); 7:65 (2H, d); 7.52 (1H, d); 7.31 (1H, d); 7.17 (2H, d); 6.77 (1H, d); 4.39 (2H, q); 2.83 (2H, t); 2.66 (2H, t); 1.37 (3H, t). IR (Nujol) (cm$^{-1}$): 3 302 and 3194 (NH,); 1676 (C=O).

EXAMPLE 6

(E)4,6-dichloro-3-[2'-(4'-aminoethylphenylcarbamoyl)ethenyl]-1H-indole-carboxylic acid sodium salt Example 5 (0.1 g) was suspended in ethanol 95% (3.5 ml) and lithium hydroxide monohydrate (0.04 g) was added. The solution was stirred at 50° for 3 hrs then acidified with a 2N aqueous solution of hydrochloric acid. The solid obtained was filtered and washed with water to afford the (E)4,6-dichloro-3-[2-(4'-aminoethyl-phenylcarbamoyl)-ethenyl]-1H-indole carboxylic acid hydrochloride which was dried under vacuum with phosphoric anhydride (0.070 mg). The solid was then suspended in water and one equivalent of a solution 0.1N of sodium hydroxide was added. The mixture was stirred for 10 min then freeze dried obtaining the title compound in mixture with 1 eq. of sodium chloride (63.8 mg)

$^1$H-NMR (DMSO): 11.82 (1H, bs); 9.98 (1H, s); 8.60 (1H; d); 7.68 (2H, d) 7.7 (bs); 7.39 (1H, d); 7.18 (2H, d); 7.16 (1H, d); 7.11 (1H, d); 3.02 (2H, t); 2.8 (2H, t). IR (Nujol) (cm$^{-1}$): 3412, 3285, 3200 (NH).

EXAMPLE 7

(E)4,6-dichloro-2-ethoxycarbonyl-3-[2'-(4'-ureidomethylphenylcarbamoyl)ethenyl]-1-H-indole Method A To a suspension of intermediate 5 (1.9 g) in ethanol (50 ml) a 2M solution of sodium hydroxide (3.2 ml) was added. The yellow solution obtained was stirred for 3 hrs at r.t., then acidified with a 2N aqueous solution of chloridric acid. The solid precipitated was filtered obtaining the title compound (1.5 g).

$^1$H-NMR (DMSO): 12.58 (1H, bs); 10.15 (bs, 1H); 8.29 (1H; d); 7,67 (2H, d) 7.51 (1H, d); 7.29 (bs); 7.21 (d); 6.77 (1H, d); 6.37 (1H, t); 5.51 (2H, bs); 4.39 (2H, q); 4.14 (2H, d); 1.37 (3H, t). IR (Nujol) (cm$^{-1}$): 3435–3246 (NH, NH$_2$); 1680–1661 (C=O); 1624–1615 (C=C).

Method B

To a solution of (E)4,6-dichloro-2-ethoxycarbonyl-3-(2'-carboxyethenyl)-indole (6 g) in dry tetrahydrofuran (150 ml), 2,2'-dipyridyl disulfide (5.64 g) and triphenylphosphine (6.71 g) were added. The reaction mixture was stirred for 4 hrs at r.t. Then intermediate 15 (3 g) in THF (30 ml) was added and the obtained mixture stirred at 50° for 2.5 hrs and at room temperature overnight. Dichloromethane was added and the obtained suspension filtered giving a solid that was triturated with dichloromethane (50 ml), filtered, and dried affording the title compound (6.6 g).

$^1$H-NMR (DMSO): 10.4 (bs, 1H); 8.09 (2H; d); 8.00 (1H, d); 7.95 (1H, d); 7.82 (1H, t); 7.70 (2H, t); 7.62 (2H, d); 7.65 (1H, d); 7.30 (1H, t); 7.18 (2H, d): 6.51 (1H, d); 4.48 (2H, q); 4.06 (2H, d); 1.40 (9H, s); 1.30 (3H, t). IR (Nujol) (cm$^{-1}$): 1730 (C=O); 1686; 1661 (C=O); 1630–1600 (C=C).

EXAMPLE 8

(E)4,6-dichloro-3-[2'-(4'-ureidomethylphenylcarbamoyl)ethenyl]-1-H-indole2-carboxylic acid Example 7 (0.119 g) was dissolved in a mixture of ethanol/water (10/2) and lithium hydroxide monohydrate (0.042 g) was added. The solution was stirred at 50° for 3 hrs then acidified at pH=3 1with a 2N aqueous solution of hydrochloric acid. The solid abtained was filtered then triturated with dichloromethane and filtered again to afford the title compound (0.060 g).

$^1$H-NMR (DMSO): 13.75 (1H, broad); 12.50 (H, s); 10.15 (s, 1H); 8.27 (1H; d); 7.65 (2H, d) 7.48 (1H, d); 7.29 (1H, d); 7.18 (2H, d); 6.80 (1H, d); 6.34 (1H, t); 5.49 (2H, bs); 4.11 (2H, d). IR (Nujol) (cm$^{-1}$): 3474, 3416 and 3265 (NH+NH$_2$); 1672 (C=O); 1609, 1582 (C=C).

EXAMPLE 9

(E)4,6-dichloro-3-[2'-(4'-ureidomethylphenylcarbamoyl)ethenyl]-1-H-indole 2-carboxylic acid,sodium salt Method A Example 8 (205 mg) was suspended in water (35 ml) and a 0.1N aqueous solution of sodium hydroxide was added. The solution was stirred for 45 min then freeze dried obtaining the title compound (210 mg).

$^1$H-NMR (DMSO): 11.8 (1H, broad); 9.97 (1H, s); 8.58 (1H; d); 7.68 (2H, d) 7.39 (1H, d); 7.19 (1H, d); 7.15 (2H, d); 7.10 (1H, d); 6.32 (1H, t); 5.47 (2H, bs); 4.10 (2H, d). IR (Nujol) (cm$^{-1}$): 3408, 3360 and 3192 (NH+NH$_2$); 1645 and 1620 (C=O).

Method B

To a suspension of example 7 (5.6 g) in isopropanol 14 (ml), NaOH (3.77 g) dissolved water (70 ml) was added in 5 min. The obtained suspension was stirred for 2 hrs at 75° then cooled to 25° C. After stirring at this temperature for 1 hr the solid was filtered, washed with a 1/5 mixture of isopropanol/water (100 ml) and dried at 60° under vacuum for 19 hrs affording the title compound (4.6 g).

$^1$H-NMR (DMSO): 11.8 (1H, broad); 9.97 (1H, s); 8.58 (1H; d); 7.68 (2H, d) 7.39 (1H, d); 7.19 (1H, d); 7.15 (2H, d); 7.10 (1H, d); 6.32 (1H, t); 5.47 (2H, bs); 4.10 (2H, d). IR (Nujol) (cm$^{-1}$): 3408, 3360 and 3192 (NH+NH$_2$); 1645 and 1620 (C=O).

EXAMPLE 10

(E)4,6-dichloro-2-ethoxycarbonyl-3-[2'-(4'-ethylureidomethylphenyl carbamoyl)ethenyl]-1-H-indole To a suspension of intermediate 6 (0.193 g) in ethanol (5 ml) a 2.5M solution of sodium hydroxide (0.24 ml) was added. The solution obtained was stirred for 3 hrs at r.t., then acidified with a 2N aqueous solution of hydrochloric acid. The solid precipitated was filtered and washed with ethanol obtaining the title compound (0.139 g).

$^1$H-NMR (DMSO): 12.60 (1H, s); 10.17 (s, 1H); 8.23 (1H; d); 7.64 (2H, d) 7.51 (1H, d); 7.32 (1H, d); 7.18 (2H, d); 6.76 (1H, d); 6.23 (1H, t); 5.84 (1H, t); 4.37 (2H, q); 4.13 (2H, d); 3.01 (2H, dq); 1.34 (3H, t); 0.98 (3H, t). IR (Nujol) (cm$^{-1}$): 3306 (NH); 3250–3350 (NH); 1676, 1661 and 1625 (C=O).

EXAMPLE 11

(E)4,6-dichloro-3-[2'-(4'-ethylureidomethylphenylcarbamoyl)ethenyl]-1-H-indole 2-carboxylic acid Example 10 (0.132 g) was dissolved in ethanol (4.2 ml) and lithium hydroxide monohydrate (0.044 g) was added. The solution was stirred at 50° for 5 hrs then acidified with a 2N aqueous solution of hydrochloric acid. The solid obtained was filtered and washed with ethanol to afford the title compound (0.072 mg; m.p.:>250° C.).

$^1$H-NMR (DMSO): 13.37 (1H, broad); 12.52 (1H, s); 10.16 (s, 1H); 8.26 (1H; d); 7.64 (2H, d) 7.48 (1H, d); 7.30 (1H, d); 7.18 (2H, d); 6.78 (1H, d); 6.22 (1H, t); 5.84 (1H, t); 4.13 (2H, d); 3.19 (2H, m); 0.98 (3H, t). IR (Nujol) (cm$^{-1}$): 3321 (NH); 1704 (C=O).

EXAMPLE 12

(E)4,6-dichloro-3-[2'-(4'-ethylureidomethylphenylcarbamoyl)ethenyl]-1-H-indole 2-carboxylic acid,sodium salt Example 11 (60 mg) was suspended in water (9.6 ml) and a 0.1N aqueous solution of sodium hydroxide (1.26 ml) was added. The solution was stirred for 45 min then freeze dried, obtaining the title compound (62 mg).

¹H-NMR (DMSO): 11.77 (1H, broad); 9.97 (1H, bs); 8.58 (1H; d); 7.67 (2H, m) 7.39 (1H, d); 7.19 (1H, d); 7.14 (2H, m); 7.09 (1H, d); 6.21 (1H, t); 5.83 (1H, t); 4.12 (2H, d); 3.02 (2H, m); 0.92 (3H, t). IR (Nujol) (cm⁻¹): 3315 (NH); 1 599 (C=O, C=C).

EXAMPLE 13

(E)4,6-dichloro-2-ethoxycarbonyl-3-[2'-(4'-ethylthioureidomethylphenyl carbamoyl)ethenyl]-1-H-indole To a suspension of intermediate 7 (0.155 g) in ethanol (3.5 ml) a 2M solution of sodium hydroxide (0.24 ml) was added. The solution obtained was stirred for 2 hrs at r.t., then acidified with a 2N aqueous solution of hydrochloric acid. The solid precipitated was filtered and washed with ethanol obtaining the title compound (0.095 g).

¹H-NMR (DMSO): 12.60 (1H, s); 10.19 (s, 1H); 8.23 (1H; d); 7.74 (1H, bm); 7.65 (2H, d); 7.50 (1H, d); 7.45 (1H, bm), 7.32 (1H, d); 7.23 (2H, d); 6.76 (1H, d); 4.58 (2H, bs); 4.37 (2H, q); 3.2–3.4 (2H); 1.34 (3H, t); 1.05 (3H, t). IR (Nujol) (cm⁻¹): 3300–3400, 3304 (NH); 1678 (C=O).

EXAMPLE 14

(E)4,6-dichloro-3-[2'-(4'-ethylthioureidomethylphenylcarbamoyl)ethenyl]-1-H-indole 2-carboxylic acid Example 13 (0.095 g) was dissolved in ethanol (2 ml) and lithium hydroxide monohydrate (0.031 g) was added. The solution was stirred at 50° for 5 hrs then acidified with a 2N aqueous solution of hydrochloric acid. The solid obtained was filtered and washed with ethanol to afford the title compound (0.027 g; ).

¹H-NMR (DMSO): 13.73 (1H, broad); 12.54 (1H, bs); 10.18 (bs, 1H); 8.26 (1H; d); 7.65 (2H, d) 7.48 (1H, d); 7.31 (1H, d); 7.23 (2H, d); 7.78–7.4 (2H, m); 6.77 (1H, d); 4.58 (2H, m); 3.32 (2H); 1.06 (3H, t). IR (Nujol) (cm⁻¹): 3290, 3196 (NH); 1712, 16664 (C=O).

EXAMPLE 15

(E)4,6-dichloro-2-ethoxycarbonyl-3-[2'-(4'-phenylureidomethylphenyl carbamoyl)ethenyl]-1-H-indole To a suspension of example 1 (0.1 g) in dry tetrahydrofuran (2 ml). Phenylisocyanate (0.097 ml) was added and the reaction mixture was stirred at 50° for 3 hrs. The solvent was evaporated and the orange solid was filtered and washed with diethylether obtaining the title compound (113 g; m.p.>250°)

¹H-NMR (DMSO): 12.58 (1H, bs); 10.18 (s, 1H); 8.50 (1H; s); 8.24 (1H, d); 7.67 (2H, d); 7.51 (1H, d); 7.39 (2H, d); 7.25(2H, d); 7.20 (2H, t); 6.87 (1H, t); 6.77 (1H, d); 6.53 (1H, t); 4.37 (2H, q); 4.24 (2H, d); 1.34 (3H, t). IR (Nujol) (cm⁻¹): 3312, 3238 (NH); 1682–1659 (C=O).

EXAMPLE 16

(E)4,6-dichloro-3-[2'-(4'-phenylureidomethylphenylcarbamoyl)ethenyl]-1-H-indole 2-carboxylic acid To a suspention of example 15 (0.110 g) in ethanol (3.0 ml), lithium hydroxide monohydrate (0.033 g) was added. The solution was stirred at 50° for 2 hrs then acidified with a 2N aqueous solution of hydrochloric acid. The solid obtained was filtered and washed with ethanol to afford the title compound (0.080 g).

¹H-NMR (DMSO): 13.73 (1H, broad); 12.54 (1H, s); 10.19 (s, 1H); 8.52 (1H; s); 8.26 (1H, d); 7.67 (2H, d) 7.48 (1H, d); 7.39 (2H, d); 7.25 (2H, d); 7.21 (2H, t); 6.88 (1H, t); 6.78 (1H, d); 6.55 (1H, t); 4.24 (2H, d). IR (Nujol) (cm⁻¹): 3302–3184 (NH); 1659–1637 (C=O).

EXAMPLE 17

(E)4,6-dichloro-3-[2'-(4'-ureidoethylphenylcarbamoyl)ethenyl]indole-carboxylic acid, ethyl ester To a suspension of example 4 (0.2 g) in dry tetrahydrofuran (80 ml), triethylamine was added (0.059 ml). The mixture was stirred for 0.5 hr at r.t. then trimethylsilylisocyanate (0.74 ml) was added and the reaction mixture was stirred at r.t. for 6 hrs. The solid was filtered and washed with diethylether obtaining the title compound (0.17 g)

¹H-NMR (DMSO): 12.56 (1H, bs); 10.14 (s, 1H); 8.23 (1H; d); 7.62 (12, d); 7.50 (1H, d); 7.32 (1H, t); 7.14 (2H, t); 6.75 (1H, d); 5.58 (1H, t); 5.40 (2H, bs); 4.37 (2q); 3.16 (2H, m); 2.61 (2H, t); 1.34 (3H, t). IR (Nujol) (cm⁻¹): 3431–3306 (NH); 1678 (C=O); 1657 (C=O).

EXAMPLE 18

4,6-dichloro-3-[(E)-2'-(4'-ureidoethylphenylcarbamoyl)ethenyl]1-H-indole2-carboxylic acid To a suspension of example 17 (0.085 g) in a mixture of ethanol/water (10/2) lithium hydroxide monohydrate (0.029 g) was added, The solution was stirred at 50° for 2 hrs then acidified at with a 2N aqueous solution of hydrochloric acid The solid obtained was filtered then triturated with dichloromethane and filtered again to afford the title compound (0.064 g).

¹H-NMR DMSO): 13.71 (1H, bs); 12.54 (1H, s); 10.13 (s, 1H); 8.24 (1H; d); 7,62 (2H, d) 7.48 (1H, d); 7.30 (1H, d); 7.14 (2H, d),; 6.76 (1H, d); 5.88 (1H, bt); 5.40 (2H, bs); 3.16 (2H, q); 2.61 (2H, t). IR (Nujol) 3504, 3362 and 3277 (NH+NH₂); 1670 (C=O).

EXAMPLE 19

4,6-dichloro-3-[(E)-2'-(4'-ureidoethylphenylcarbamoyl)ethenyl]-1-H-indole 2-carboxylic acid,sodium salt Example 18 (40 mg) was suspended in water (6 ml) and a 0.1N aqueous solution of sodium hydroxide is added. The solution was stirred for 1.5 hrs then freeze dried obtaining the title compound (41 mg).

¹H-NMR (DMSO): 11.75 (1H, bs); 9.94 (1H, s); 8.57 (1H; d); 7.66 (2H, d) 7.39 (1H, d); 7.20 (1H, d); 7.10 (2H, d); 7.09 (1H; d); 5.88 (1H, bt); 5.41 (2H, bs); 3.14 (2H, m); 2.60 (2H, m). IR (Nujol) (cm.⁻¹): 3325 (NH+NH₂); 1657 and 1609 (C=O).

EXAMPLE 20

(E)4,6-dichloro-3-[2'-(4'-ureido-phenylcarbamoyl)-ethenyl]1H-indole-2-carboxylic acid ethyl ester A 2M solution of sodium hydroxide (0.162 ml) was added to a suspension of intermediate 14 (0.102 g) in ethanol (4 ml;

95%). The yellow solution obtained was stirred at r.t. for 2 h then acidified with a 2N solution of hydrochloric acid. The solid precipitated was filtered and washed with ethyl acetate to give the title compound (0.055 g) as a solid.

$^1$H-NMR (DMSO): 12.59 (bs), 10.06 (s), 8.55 (d), 8.20 (d), 7.56 (d), 7.50 (d), 7.32 (d), 7.29 (d), 6.72 (d), 5.8 (s), 4.36 (q), 1.33 (t). IR (Nujol) (cm$^{-1}$): 3400–3308 (N-H, NH$_2$); 1682, 1653 (C=O).

EXAMPLE 21

4,6-dichloro-3-[(E)-2'-(4'-ureidophenylcarbamoyl) ethenyl]-1-H-indole2-carboxylic acid, To a solution of example 20 (54.6 mg) in ethanol 95% pure (3 ml), 2M solution of sodium hydroxide (0.34 ml) was added. The solution was stirred at 50° for 2 hrs then acidified with a 1N aqueous solution of hydrochloric acid. The solid obtained was filtered and washed with water. The solid was dried under vacuum overnight to afford the title compound (14 mg). m.p.>250°.

$^1$H-NMR (DMSO): 12.80 (1H, s); 10.0 (1H, s); 8.43 (1H; s); 8.22 (1H, d) 7.55 (2H, d); 7.47 (1H, d); 7.32 (2H, d); 7.29 (1H, d), 6.80 (1H, d); 5.8 (2H, bs). IR (Nujol) $\nu_{max}$ (cm$^{-1}$): 3260–3190 (NH); 1684–1650 (C=O).

EXAMPLE 22

(E)-4,6-dichloro-3-[2'-(4'-ureido-phenylcarbamoyl)-ethenyl]-1H-indole-2-carboxylic acid sodium salt A 2M solution of sodium hydroxide (0.82 ml) was added to a suspension of example 20 (0.189 g) in ethanol (4 ml; 95%). The reaction mixture was stirred at 50° for 3 h then the solvent was removed under reduced pressure. Bidistilled water (10 ml) was added to the residue and the solid was filtered to give the title compound (0.167 g) as a yellow solid.

$^1$H-NMR (DMSO): 11.86 (bs), 9.96 (bs), 9.77 (s), 8.76 (d), 7.63 (d), 7.51 (d), 7.41 (d), 7.13 (d), 7.00 (d), 6.36 (bs).

EXAMPLE 23

(E)4,6-dichloro-3-[2'-(4'-phenyl-ureido-phenylcarbamoyl)ethenyl]-1H-indole-2-carboxylic acid ethyl ester A suspension of intermediate 16(0.158 g) and lithium hydroxide monohydrate (0.039 g) in ethanol (4 ml; 95%) and THF (2 ml) was stirred at r.t. for 4 h. The solution obtained was then acidified with a 1M solution of hydrochloric acid until pH=1 and the precipitate formed was filtered to give the title compound (0.110 g) as a beige solid.

$^1$H-NMR (DMSO): 12.61 (bs), 10.14 (bs), 8.73 (s), 8.71 (s), 8.24 (d), 7.65 (d), 7.53 (d), 7.46 (dd), 7.42 (d), 7.34 (d), 7.28 (t), 6.97 (tt), 6.77 (d), 4.41 (q), 1.37 (t). IR (Nujol) (cm$^{-1}$): 3310 (N—H); 1676, 1657 (C=O); 1624 (C=C).

EXAMPLE 24

(E)-4,6-dichloro-3-[2'-(4'-phenyl-ureido-phenylcarbamoyl)ethenyl]-1H-indole-2-carboxylic acid To a solution of example 23 (0.095 g), lithium hydroxide monohydrate (0.030 g) in ethanol (3 ml; 95%) was stirred at 50° C. for 5 h. After cooling to r.t. the solution was acidified with a 2M solution of hydrochloric acid until pH=1 and the precipitate formed was filtered to give the title compound (0.063 g) as a yellow solid.

$^1$H-NMR (DMSO): 13.80 (bs), 12.52 (bs), 10.11 (bs), 8.66 (bs), 8.26 (d), 7.63 (d), 7.48 (d), 7.5–7.6 (m), 7.30 (d), 7.29 (t), 6.94 (dt), 6.77 (d). IR (Nujol) (cm$^{-1}$): 2720 (N—H); 1653 (C=O, C=C).

EXAMPLE 25

(E)-4,6-dichloro-3-[2'-(4'-phenyl-ureido-phenylcarbamoyl)ethenyl]-1H-indole-2-carboxylic acid sodium salt Aqueous sodium hydroxide (1.15 ml; 0.1N) was added to a suspension of example 23 (0.059 g) in bidistilled water (5 ml). The suspension was stirred at r.t. for 30 min then was freeze-dried to give the title compound (0.061 g) as a yellow solid.

$^1$H-NMR (DMSO): 11.92 (bs), 11.62 (broad), 10.65,(bs), 9.80 (bs), 8.94 (d), 7.76 (m), 7–49 (m), 7.23 (m), 7.18 (m) 6.89 (m). IR (Nujol) (cm$^{-1}$): 3315 (N—H); 1720, 1595 (C=O, C=C).

EXAMPLE 26

(E)-4,6-dichloro-3-[2'-(4'-dimethyl-ureido-phenylcarbamoyl)ethenyl]-1H-indole-2-carboxylic acid ethyl ester A 2M solution of sodium hydroxide (0.150 ml) was added to a suspension of intermediate 17(0.096 g) in ethanol (3 ml; 95%). Addition of THF (2 ml) to the reaction mixture gave a solution that was stirred at r.t. for 1 h. A 2N solution of hydrochloric acid was then added until a solid precipitated. The precipitate was filtered to give the title compound (0.074 g) as a yellow solid.

$^1$H-NMR (DMSO): 12.58 (s), 10.06 (s), 8.21 (s), 8.20 (d), 7.56 (d), 7.50 (d), 7.38 (d), 7.31 (d), 6.73 (d), 4.37 (q), 2.90 (s), 1.34 (t). IR (Nujol) (cm$^{-1}$): 3310 (N—H); 1678, 1659 (C=O).

EXAMPLE 27

(E)-4,6-dichloro-3-[2'-(4'-dimethyl-ureido-phenylcarbamoyl)ethenyl]-1H-indole-2-carboxylic acid A suspension of example 26 (0.070 g) and lithium hydroxide monohydrate (0.024 g) in ethanol (2 ml; 95%) was stirred at 50° for 3.5 h. After cooling to r.t. the solution was acidified with a 2M solution of hydrochloric acid until a solid precipitated. The precipitate was filtered to give the title compound (0.0659 g) as a pale orange solid.

$^1$H-NMR (DMSO): 13.7 (bs), 12.52 (bs), 10.06 (bs), 8.22 (d), 8.21 (bs), 7.59 (m), 7.47 (d), 7.38 (m), 7.29 (d), 6.75 (d), 2.90 (s). IR (Nujol) (cm$^{-1}$): 3234 (N—H); 1686, 1659 (C=O); 1620 (C=O, C=C).

EXAMPLE 28

(E)-4,6-dichloro-3-[-2'-(4'-dimethyl-ureido-phenylcarbamoyl)ethenyl]-1H-indole-2-carboxylic acid sodium salt Aqueous sodium hydroxide (1.3 ml; 0.1N) was added to a suspension of example 27 (0.060 g) in bidistilled water (5 ml). The suspension was stirred at r.t. for 1 h then was freeze-dried to give the title compound (0.062 g) as a pale yellow solid.

$^1$H-NMR (DMSO): 11.8 (bs), 9.87 (s), 8.54 (d), 8.16 (s), 7.58 (d), 7.40 (d), 7.33 (d), 7.16 (d), 7.09 (d), 2.89 (s). IR (Nujol) (cm$^{-1}$): 3377, 3321, 3184 (N—H); 1653, 1600 (C=O, C=C).

EXAMPLE 29

(E)-4,6-dichloro-3-[-2'-(4'-cyclopropyl-ureido-methyl-phenylcarbamoyl)vinyl]-1H-indole-2-carboxylic acid ethyl ester Triethylamine (0.81 ml) and diphenylphosphoryl azide (1.25 ml) were added to a solution of cyclopropane carboxylic acid (0.46 ml) in dry toluene (4 ml) at 0° C. The reaction mixture was stirred at r.t. for 3 h and heated at 80° C. for 3.5 h then allowed to cool to r.t. A portion (2 ml) was taken and added to a suspension of intermediate 4 (0.200 g) and triethylamine (0.061 ml) in dry THF (8 ml) previously stirred at r.t. for 1 h. The reaction mixture was stirred at r.t. overnight then diluted with water and extracted with ethyl acetate. The organic extracts were dried and evaporated to a small volume under reduced pressure. The solid suspended was filtered to give the title compound (0.143 g) as a yellow solid.

$^1$H-NMR (DMSO): 12.61 (bs), 10.18 (bs), 8.26 (d), 7.66 (d), 7.53 (d), 7.34 (d), 7.21 (d), 6.79 (d), 6.34 (bt), 6.20 (bd), 4.40 (q), 4.18 (d), 2.44 (m), 0.59 (m), 0.36 (m). IR (Nujol) (cm$^{-1}$): 3304 (N—H); 1676, 1640 (C=O).

EXAMPLE 30

(E)-4,6-dichloro-3-[-2'-(4'-cyclopropyl-ureido-methyl-phenylcarbamoyl)vinyl]-1H-indole-2-carboxylic acid A solution of example 29 (0.070 g) and lithium hydroxide monohydrate (0.0177 g) in ethanol (2 ml, 95%) was stirred at 50° C. for 2.5 h then at r.t. ovenight. After cooling to r.t. the solution was acidified with a 2M solution of hydrochloric acid until a solid precipitated. The solvent was evaporated to a small volume under reduced pressure and the solid suspended was filtered to give the title compound (0.051 g) as a cream solid.

$^1$H-NMR (DMSO): 13.73 (bs), 12.55 (bs), 10.17 (bs), 8.26 (d), 7.64 (m), 7.48 (d), 7.30 (d), 7.19 (m), 6.77 (d), 6.32 (bt), 6.18 (bd), 4.16 (d), 2.40 (m), 0.56 (m), 0.33 (m). IR (Nujol) (cm$^{-1}$): 3500–2300 (O—H, N—H); 1650, 1620 (C=O); 1601 (C=C).

EXAMPLE 31

(E)-4,6-dichloro-3-[-2'-(4'-cyclopropyl-ureido-methyl-phenylcarbamoyl)vinyl]-1H-indole-2-carboxylic acid sodium salt Aqueous sodium hydroxide (0.57 ml; 0.1N) was added to a suspension of example 30 (0.028 g) in bidistilled water (6 ml). The suspension was stirred at r.t. for 2.5 h then was freeze-dried to give the title compound (0.029 g) as a yellow solid.

$^1$H-NMR (DMSO): 11.80 (bs), 9.99 (bs), 8.57 (d), 7.67 (d), 7.40 (d), 7.18 (d), 7.14 (d), 7.09 (d), 6.30 (bt), 6.18 (bd), 4.13 (d), 2.41 (m), 0.55 (m), 0.33 (m). IR (Nujol) (cm$^{-1}$): 3327 (N—H); 1700, 1661 (C=O); 1601 (C=C).

EXAMPLE 32

(E)-4,6-dichloro-3-[2'-(3'-ammonium-methyltrifluoroacetate-phenylcarbamoyl)-ethenyl]-1H-indole-2-carboxylic acid isopropyl ester Trifluoroacetic acid (1.28 ml) was added to a stirred suspension of intermediate 21 (0.283 g) in dichloromethane (3 ml). The reaction mixture was stirred at r.t. for 2 h then the solvent was removed under reduced pressure. The oil obtained was repeatedly treated with diethyl ether and dried on the rotary evaporator to remove any residue of trifluoroacetic acid. Trituration with diethyl ether and filtration of the solid obtained gave the title compound (0:264 g) as a white. solid.

$^1$H-NMR (DMSO): 12.56 (bs), 10.31 (bs), 8.28 (d), 8.14 (bs), 7.98 (bs), 7.56 (m), 7.52 (d), 7.38 (t), 7.32 (d), 7.15 (d), 6.77 (d), 5.19 (m), 4.01 (s), 1.34 (d). IR (Nujol) (cm$^{-1}$): 3412, 3254 (N—H); 3200–2500 (NH$_3^+$); 1672 (C=O); 1630, 1612 (C=O, C=C).

EXAMPLE 33

(E)-4,6-dichloro-3-[2'-(3'-ureidomethyl)-phenylcarbamoyl)-ethenyl ]-1H-indole-2-carboxylic acid isopropyl ester A suspension of example 32 (0.247 g) and triethylamine (0.074 ml) in dry THF (9 ml) was stirred at r.t. for 1 h then trimethylsilylisocyanate (0.140 ml; 85%) was added. The reaction mixture was stirred at r.t. for 2 h then the solvent was removed under reduced pressure. The residue was repeatedly treated with diethyl ether and dried on the rotary evaporator. Trituration with diethyl ether and filtration of the solid obtained gave the title compound (0.211 g) as an off white solid $^1$H-NMR (DMSO): 12.55 (bs), 10.21 (s), 8.24 (d), 7.63 (m), 7.61 (s), 7.53 (d), 7.34 (d), 7.27 (t), 6.95 (d), 6.75 (d), 6.43 (t), 5.54 (s), 5.20 (m), 4.17 (d), 1.36 (d). IR (Nujol) (cm$^{-1}$): 3416, 3400, 3244, 3204 (N—H); 1682, 1666 (C=O); 1610 (C=C).

EXAMPLE 34

(E)-4,6-dichloro-3-[2'-(3'-ureidomethyl)-phenylcarbamoyl)-ethrnyl)]-1H-indole-2-carboxylic acid A suspension of example 33 (0.100 g) and lithium hydroxide monohydrate (0.026 g) in ethanol (2 ml; 95%) was stirred at 50° for 5.5 h. After cooling to r.t. the solution was acidified with a 2M solution of hydrochloric acid until a solid precipitated. The precipitate was filtered to give the title compound (0.076 g) as a yellow solid.

$^1$H-NMR (DMSO): 13.73 (bs), 12.54 (s), 10.20 (s), 8.26 (d), 7.61 (d), 7.58 (bs), 7.48 (d), 7.30 (d), 7.24 (t), 6.92 (d), 6.78 (d), 6.39 (t), 5.51 (bs), 4.15 (d). IR (Nujol) (cm$^{-1}$): 3267 (N—H); 1672 (C=O); 1620 (C=C).

EXAMPLE 35

(E)-4,6-dichloro-3-[2'-(3'-ureidomethyl)-phenylcarbamoyl)-ethenyl]-1H-indole-2-carboxylic acid sodium salt Aqueous sodium hydroxide (1.34 ml; 0.1N) was added to a solution of example 34 (0.060 g) in bidistilled water (10 ml). The solution was stirred at r.t. for 1 h then was freeze-dried to give the title compound (0.062 g) as a pale yellow solid.

$^1$H-NMR (DMSO): 11.82 (bs), 10.03 (s), 8.59 (d), 7.7–7.6 (bm), 7.41 (d), 7.203 (t), 7.20 (d), 7.10 (d), 6.88 (d), 6.39 (bs), 5.51 (bs), 4.13 (d). IR (Nujol) (cm$^{-1}$): 3341 (N—H); 1653, 1607 (C=O); 1551 (C=C).

EXAMPLE 36

(E)-4,6-dichloro-3'-{2'-[4'-(4"-methoxy-phenyl-ureidomethyl)-phenyl carbamoyl]ethenyl}-1H-indole-2-carboxylic acid ethyl ester 4-Methoxyphenyl isocyanate (0.116 ml) was added to a suspension of example 1 (0.100 g) in dry THF (2 ml). The reaction mixture was stirred at 70° C. for 3 h then left at r.t. for 2 days. The precipitate formed was filtered and washed with ethyl acetate and diethyl ether to give the title compound (0.100 g) as a white solid.

$^1$H-NMR (DMSO): 12.59 (bs), 10.17 (bs), 8.30 (bs), 8.24 (d), 7.67 (d), 7.51 d), 7.32 (d), 7.29 (m), 7.24 (d), 6.80 (m), 6.77 (d), 6.43 (t), 4.38 (q), 4.23 (d), 3.68 (s), 1.35 (t). IR (Nujol) (cm$^{-1}$): 3302 (N—H); 1676–1624 (C=O, C=C).

EXAMPLE 37

(E)-4,6-dichloro-3-{2'-[4'-(4"-methoxy-phenyl-ureidomethyl)-phenyl carbamoyl]ethenyl}-1H-indole-2-carboxylic acid A solution of example 36 (0.100 g) and lithium hydroxide monohydrate (0.029 g) in ethanol (2.5 ml; 95%) was stirred at 50° for 3.5 h. After cooling to r.t. the reaction mixture was acidified with a 2M solution of hydrochloric acid (0.6 ml) and stirred at r.t for 30 min. The precipitate was filtered to give the title compound (0.070 g) as an off white solid.

$^1$H-NMR (DMSO): 13.73 (bs), 12.55 (s), 10.19 (s), 8.32 (s), 8.26 (d), 7.67 (d), 7.48 (m), 7.31 (m), 7.29 (d), 7.24 (d), 6.80 (d), 6.78 (d), 6.44 (t), 4.23 (d), 3.68 IR (Nujol) (cm$^{-1}$): 3400–3200 (N—H); 1650 (C=O).

EXAMPLE 38

(E)-4,6-dichloro-3-[2'-4'-tetrahydro-pyran-4"-yl-ureido-methyl)-phenylcarbamoyl)-ethenyl]-1H-indole-2-carboxylic acid ethyl ester Triethylamine (0.214 ml) and diphenylphosphoryl azide (0.33 ml) were added to a solution of tetrahydropyran-4-carboxylic acid (0.200 g) in dry toluene (2 ml) at 0°. The reaction mixture was stirred at r.t. for 2 h and heated at 80° for 1.5 h then allowed to cool to r.t. A portion (1 ml) was taken and added to a suspension of example 4 (0.180 g) and triethylamine (0.050 ml) in dry THF (4 ml) previously stirred at r.t. for 20 min. The reaction mixture was stirred at r.t. overnight then the solvent was removed under reduced pressure. The residue was suspended in ethyl acetate and washed with water then the solid suspended in the organic extracts was filtered to give the title compound (0.163 g) as a white solid.

$^1$H-NMR (DMSO): 12.61 (s), 10.18 (s), 8.26 (d), 7.67 (d), 7.53 (d), 7.34 (d), 7.21 (d), 6.79 (d), 6.18 (t), 5.95 (d), 4.40 (q), 4.17 (d), 3.80 (dt), 3.60 (m), 3.36 (dt), 1.74 (m), 1.37 (ft), 1.32 (m). IR (Nujol) (cm$^{-1}$); 3296 (N—H); 1676, 1661, 1630 (C=O).

EXAMPLE 39

(E)-4,6-dichloro-3-[2'-(4'-tetrahydro-pyran-4"-yl-ureido-methyl)-phenylcarbamoyl)-ethenyl ]-1H-indole-2-carboxylic acid A solution of example 38 (0.080 g) and lithium hydroxide monohydrate (0.024 g) in ethanol (2 ml; 95%) was stirred at 50° C. for 4 h. After cooling to r.t. the reaction mixture was acidified with a 2M solution of hydrochloric acid until a solid precipitated. The precipitate was filtered to give the title compound (0.064 g) as a yellow solid.

$^1$H-NMR (DMSO): 13.74 (bs), 12.55 (bs), 10.17 (bs), 8.26 (d), 7.64 (m), 7.48 (d), 7.30 (d), 7.18 (m), 6.78 (d), 6.17 (bt), 5.94 (bd), 4.14 (d), 3.78 (m), 3.57 (m), 3.32 (m), 1.72 (m), 1.30 (m).

IR (Nujol) (cm$^{-1}$): 3500–2200 (O—H, N—H); 1661, 1626 (C=O).

EXAMPLE 40

(E)-4,6-dichloro-3-[2'-(4'-tetrahydro-pyran-4"-yl-ureido-methyl)-phenylcarbamoyl)-ethenyl]-1H-indole-2-carboxylic acid sodium salt Aqueous sodium hydroxide (0.87 ml; 0.1N) was added to a suspension of example 39 (0.046 g) in bidistilled water (6 ml). The solution obtained was stirred at r.t. for 2.5 h then was freeze-dried to give the title cot pound (0.046 g) as a pale yellow solid.

$^1$H-NMR (DMSO): 11.75 (broad), 9.94 (s), 8.59 (d), 7.67 (d), 7.37 (d), 7.18 (d), 7.14 (d), 7.09 (bs), 6.14 (t), 5.92 (d), 4.12 (d), 3.77 (m), 3.58 (m), 3.3 (r), 1.72 (m), 1.29 (m). IR (Nujol) (cm$^{-1}$): 3312 (N—H); 1622 (C=O).

EXAMPLE 41

(E)-4,6-dichloro-3-[2'-(4'-nicotin-3'-yl-ureido-methyl-phenylcarbamoyl)-ethenyl]-1H-indole-2-carboxylic acid ethyl ester Triethylamine (0.226 ml) and diphenylphosphoryl azide (0.3 ml) were added to a suspension of nicotinic acid (0.200 g) in dry toluene (3 ml) at 0°. The reaction mixture was stirred at r.t. for 2 h then was filtered through a plug of silica using ethyl acetate as eluant. The solvent was removed under reduced pressure to give a white solid that was dissolved in dry toluene (5 ml). The solution was stirred at 80° for 2.5 h and allowed to cool to r.t., then was added to a suspension of example 4 (0.150 g) and triethylamine (0.042 ml) in dry THF (3 ml) previously stirred at r.t. for 30 min. The reaction mixture was left at r.t. for 2 days and the precipitate formed was filtered and washed with diethyl ether. The solid was then adsorbed onto silica and eluted through a short column of silica using ethyl acetate/ethanol 9:1 as eluant. The solvent was removed under reduced pressure and the residue was triturated in ethanol to give after filtration the title compound (0.040 g) as a yellow solid.

$^1$H-NMR (DMSO): 12.61 (bs), 10.21 (bs), 8.75 (bs), 8.55 (d), 8.27 (d), 8.12 (dd), 7.91 (m), 7.70 (d), 7.53 (d), 7.34 (d), 7.28 (d), 7.26 (m), 6.79 (d), 6.74 (bt), 4.40 (q), 4.28 (d), 1.37 (t). IR (Nujol) (cm$^{-1}$): 3304, 3244 (N—H); 1700–1610 (C=O, C=N, C=C).

EXAMPLE 42

(E)-4,6-dichloro-3-[2'-(4'-nicotin-3'-yl-ureido-methyl-phenylcarbamoyl)-ethenyl]-1H-indole-2-carboxylic acid Lithium hydroxide monohydrate (0.013 g) was added to a suspension of example 41 (0.040 g) in ethanol (1.5 ml; 95%). The reaction-mixture was refluxed for2.5 h then cooled to r.t. and acidified with a 2N solution of hydrochloric acid (0.1 ml). The solid precipitated was filtered to give the title compound (0.010 g) as a white solid.

$^1$H-NMR (DMSO): 13.73 (bs), 12.51 (s), 10.17 (s), 8.73 (s), 8.52 (d), 8.26 (d), 8.10 (dd), 7.89 (ddd), 7.66 (d), 7.47 (d), 7.29 (d), 7.24 (d), 6.79 (d), 6.73 (t), 4.25 (d). IR (Nujol) 1 (cm$^{-1}$): 3206 (N—H); 1696, 1653 (C=O); 1609 (C=C).

EXAMPLE 43

(E)-4,6-dichloro-3-[2'-(4'-ethoxycarbonylmethyl-ureido-methyl)-phenylcarbamoyl)ethenyl]1-1H-indole-2-carboxylic acid ethyl ester Ethyl isocyanatoacetate (0.061 ml) was added to a suspension of example 2(0.150 g) and triethylamine (0.042 ml)

in dry THF (5 ml) previously stirred at r.t. for 20 min. The reaction mixture was stirred at r.t. for 2.5 h and the precipitate formed was filtered and washed with diethyl ether to give the title compound (0.130 g) as a yellow solid.

$^1$H-NMR (DMSO): 12.61 (bs), 10.17 (s), 8.23 (d), 7.64 (d), 7.50 (d), 7.32 (d), 7.19 (d), 6.76 (d), 6.61 (t), 6.25 (t), 4.37 (q), 4.15 (d), 4.07 (q), 3.77 (d), 1.78 (t), 1.34 (t). IR (Nujol) (cm$^{-1}$): 3302 (N—H); 1678 (C=O).

EXAMPLE 44

(E)-4,6-dichloro-3-[2'-(4'-carboxymethyl ureido-methyl-phenylcarbamoyl)ethenyl]-1H-indole-2-carboxylic acid Lithium hydroxide monohydrate (0.030 g) was added to a suspension of example 43 (0.050 g) in THF (3 ml) and H$_2$O (1 ml). The dark solution obtained was stirred at 40° C. for 6 h then cooled to r.t. and acidified with a 2N solution of hydrochloric acid until a solid precipitated. The precipitate was filtered to give the title compound (0.025 g) as a brown solid.

$^1$H-NMR (DMSO): 13.8 (broad), 12.54 (bs), 10.18 (bs), 8.25 (d), 7.64 (d), 7.48 (d), 7.30 (d), 7.18 (d), 6.77 (d), 6.59 (bs): 6.16 (broad), 4.15 (s), 3.71 (s). IR (Nujol) (cm$^{-1}$) 3400–2500 (O—H, N—H); 1661 (C=O), 1610 (C=O, C=C).

EXAMPLE 45

4,6-dichloro-2-ethoxycarbonyl-3-[(E)-2'-(4'-ethylureidophenylcarbamoyl) ethenyl]-1-H-indole To a suspension of intermediate 22 (230 mg) in a mixture of ethanol 95% pure (10 ml), water (1.5 ml) and THF (4 ml) a 2M solution of sodium hydroxide (0.365 ml) was added. The yellow solution obtained was stirred for 2 hrs at r.t., then acidified with a 2N aqueous solution of hydrochloric acid. The solid precipitated was filtered, washed with water and dried under vacuum to obtain the title compound (160 mg). m.p.>250°.

$^1$H-NMR (DMSO): 12.57 (1H, bs); 10.03 (1H, bs); 8.33 (1H; bs); 8.20 (1H, d), 7.55 and 7.49 (3H, m and d), 7.31 and 7.30 (1H, m and d); 6.72 (1H, d); 6.03 (1H, t), 4.37 (2H, q); 3.07 (2H, m), 1.34 (3H, t), 1.03 (3H, t). IR (Nujol) $v_{max}$ (cm$^{-1}$): 3304–3238 (NH); 1678–1650–1620 (C=O).

EXAMPLE 46

4,6-dichloro-3-[(E)-2'-(4'-ethylureidophenylcarbamoyl)ethenyl]-1-H-indole-2-carboxylic acid To a solution of example 45 (119 mg) in ethanol 95% pure ml), water (0.6 ml), a 2M solution of sodium hydroxide (0.487 ml) was added. The solution was stirred at 50° for 4 hrs then acidified with a 0.1N aqueous solution of hydrochloric acid. The solid obtained was filtered and washed with water. The solid was dried under vacuum overnight and triturated with isopropanol to afford the title compound (41 mg). m.p.>250°.

$^1$H-NMR (DMSO): 13.55 (1H, broad), 12.48 (1H, bs); 10.03 (1H, bs); 8.36 (1H; bs); 8.24 (1H, d) 7.55 (2H, d); 7.47 (1H, d); 7.31 (2H, d); 7.28 (1H, d), 6.77 (1H, d); 6.06 (1H, m), 3.06 and 1.03 (2H and 3H under solvent signal). IR (Nujol) $v_{max}$ (cm$^{-1}$): 3302 (NH and OH); 1684–1640 (C=O), 1610 (C=C).

EXAMPLE 47

4,6-dichloro-2-ethoxycarbonyl-3-[(E)-2'-(4'-cyclohexylureidolphenylcarbamoyl)ethenyl]-1-H-indole To a suspension of intermediate 23 (170 mg) in a mixture of ethanol 95% pure (5 ml), water (0.7 ml) and THF (4 ml) a 2M solution of sodium hydroxide (0.249 ml) was added. The yellow solution obtained was stirred for 4 hrs at r.t., then acidified with a 0.1N aqueous solution of hydrochloric acid. The solid precipitated was filtered, washed with water and dried under vacuum to obtain the title compound (110 mg). m.p.>250°.

$^1$H-NMR (DMSO): 12.59 (1H, bs); 10.06 (1H, bs); 8.24 (1H; s); 8.22 (1H, d), 7.58 (2H, d), 7.53 (1H, d), 7.34 (1H, d), 7.32 (2H, d); 6.75 (1H, d); 6.03 (1H, d), 4.40 (2H; q); 3.47 (1H, m), 1.80 (2H, m), 1.67 (2H, m), 1.53 (1H, m), 1.35 t), 1.28 (2H, m), 1.26–1.1 (3H, m). IR (Nujol) $v_{max}$ (cm$^{-1}$): 3304 (NH); 1678 (C=O), 1630–1610 (C=C).

EXAMPLE 48

4,6-dichloro-3-[(E)-2'-(4'-cyclohexylureidophenylcarbamoyl)ethenyl]-1-H-indole-2-carboxylic acid sodium salt To a solution of example 47 (102 mg) in ethanol 95% pure (4 ml), water (0.6 ml), THF (1 ml) and a 2M solution of sodium hydroxide (0.375 ml) was added. The solution is stirred at 50° for 6 hrs then acidified with a 0.1N aqueous solution of hydrochloric acid. The solid obtained was filtered and washed with water. The solid was dried under vacuum overnight, dissolved in a 0.1M solution of sodium hydroxide (1.30 ml) and water and freeze dried to afford the title compound (72 mg).

$^1$H-NMR (DMSO): 12.01 (1H, bs); 9.82 (1H, bs); 9.52 (1H; bs); 8.63 (1H, bd) 7.62–7.46–7.45 (5H, m–m–d), (2H, d); 7.18 (1H, d), 6.87 (1H, d); 7.1–6.8 (1H, broad), 3.43 (1H, m), 1.80–1.45 and 1.40–1.00 (1 OH, m and m). IR (Nujol) $v_{max}$ (cm$^{-1}$): 3500 (NH); 1653–1620 (C=O).

EXAMPLE 49

4,6-dichloro-2-ethoxycarbonyl-3-[(E)-2'-(4'-cyclopropylureidophenylcarbamoyl)ethenyl]-1-H-indole To a suspension of intermediate 24 (120 mg) in a mixture of ethanol 95% pure (5 ml), water (0.7 ml) and THF (2 ml) a 2M solution of sodium hydroxide (0.187 ml) was added. The yellow solution obtained was stirred for 4 hrs at r.t., then acidified with a 0.1N aqueous solution of chloridric acid. The solid precipitated was filtered, washed with water and ethylacetate and dried under vacuum to obtain the title compound (81 mg). m.p.>250°.

$^1$H-NMR (DMSO): 12.57 (1H, bs); 10.05 (1H, bs); 8.21 (1H; bs); 8.20 (1H, d), 7.56 (2H, m), 7.50 (1H, d), 7.32 (1H, m), 7.31 (2H, d); 6.73 (1H, d); 6.32 (1H, bd) 4.37 (2H, q); 2.51 (1H, m), 1.34 (3H, t), 0.61 (2H, m), 0.38 (2H, m). IR (Nujol) $v_{max}$ (cm$^{-1}$): 3310 (NH); 1678–1645 (C=O), 1620 (C=C).

EXAMPLE 50

4,6-dichloro-3-[(E)-2'-(4'-cyclopropylureidophenylcarbamoyl)ethenyl]-1-H-indole-2-carboxylic acid sodium salt To a solution of example 49(44 mg) in ethanol 95% pure (3 ml) and water (0.3 ml) and litium hydroxide-monohydrate (15 mg) was added. The solution was stirred at 50° for 5 hrs then acidified with a 0.1N aqueous solution of hydrochloric acid. The solid obtained was filtered and washed with water. The solid was dried under vacuum overnight to afford the title compound (20 mg). m.p.>250° C.

$^1$H-NMR (DMSO): 13.7 (1H, broad), 12.52 (1H, bs); 10.06 (1H, bs); 8.24 (1H; bs); 8.25 (1H, d) 7.59 and 7.50

(3H, d and d), 7.35 and 7.31 (3H, d and d); 6.78 (1H, d), 6.36 (1H, bs), 2.52 (1H, m), 0.64 (2H, m), 0.40 (2H, m). IR (Nujol) $v_{max}$ (cm$^{-1}$): 3412–3250 (NH, OH); 1678–1609 (C=O).

EXAMPLE 51

4,6-dichloro-3-[(E)-2'-(4'-nicotin-3-ylureidophenylcarbamoyl)ethenyl]-1-H-indole2-carboxylic acid To a solution of Intermediate 25 (63 mg) was dissolved in ethanol 95% pure (5 ml), water (0.7 ml), THF (2 ml) and a 2M solution of sodium hydroxide (0.093 ml) was added. The yellow solution obtained was stirred 3 hrs at r.t. then acidified with a 0.1N aqueous solution of hydrochloric acid. The solid obtained was filtered and washed with water to obtained 4,6-dichloro-3-[(E)-2'-(4'-nicotin-3-ylureidophenylcarbamoyl)ethenyl]-1-H-indole2-carboxylic acid ethyl ester (14 mg) which was dissolved in ethanol (3 ml) and litium hydroxide monohydrate (5 mg) was added. The solution was stirred at 50° for 4 hrs then acidified with a 0.1N aqueous solution of hydrochloric acid. The solid obtained was filtered and washed with water. The solid was dried under vacuum overnight to afford the title compound (6 mg).

$^1$H-NMR (DMSO): 12.52 (1H, s), 10.12 (1H, s), 8.80 (1H, s), 8.73 (1H, s), 8.58 (1H, d), 8.24 (1H, d), 8.16 (1H, dd), 7.93 (1H, m); 7.64 (2H, d), 7.48 (1H, d); 7.44–7.25 (3H, m), 7.30 (1H, d), 6.76 (1H, d). IR (Nujol) (cm$^{-1}$): 1607 (C=O).

EXAMPLE 52

4,6-dichloro-3-[(E)-2'-(4'-(-tetrahydropyran-4"-yl)-ureidophenylcarbamoyl)ethenyl]-1-H-indole-2-carboxylic acid sodium salt To a solution of intermediate 26(142 mg) in ethanol 95% pure (5 ml), water (0.7 ml), THF (2 ml) and a 2M solution of sodium hydroxide (0.31 ml) was added. The yellow solution obtained was stirred overnight at r.t. then acidified with a 0.1N aqueous solution of hydrochloric acid. The solid obtained was filtered and washed with water to obtain a mixture of 4,6-dichloro-3-[(E)-2'-(4'-(-tetrahydropyran-4"-yl)-ureidophenylcarbamoyl)ethenyl]-1-H-indole-2-carboxylic acid and the title compound (75 mg). The mixture was dissolved in ethanol (3 ml) and a 2M solution of sodium hydroxide (0.137 ml) was added. The solution was stirred at 50° for 4 hrs then acidified with a 0.1N aqueous solution of hydrochloric acid. The solid obtained was filtered and washed with water. The solid was dried under vacuum overnight, dissolved in a 0.1M solution of sodium hydroxide (0.74 ml) and water and freeze dried to afford the title compound (38 mg).

$^1$H-NMR (DMSO): 8.17 (1H, d) 7.18 and 7.15 (3H, d and m); 6.96 and 6.95 (3H, m and d), 6.43 (1H, d); 3.84 (2H, m), 3.59 (1H, m), 3.43 (2H, m), 1.76 (2H, m),1.37 (2H, m). IR (Nujol) $v_{max}$ (cm$^{-1}$): 3402–3310 (NH); 1607 (C=O).

Pharmacy Example

| Intravenous Infusion | % w/v |
|---|---|
| A glycine antagonist of formula (I) | 0.3–0.5 |
| Polysorbate 80 | 1 |

| Intravenous Infusion | % w/v |
|---|---|
| tris(hydroxymethyl)aminomethane | 0.54 |
| Dextrose solution 5% w/v | qs to volume |

The glycine antagonist and Polysorbate were added to a solution of tris(hydroxymethyl)aminomethane in a 5% aqueous dextrose solution suitable for injection. The solution was filtered through a sterile 0.2 micron sterlising filter and filled in containers before being sterilised by autoclaving.

The affinity of a compound of the invention for strychnine insensitive glycine binding site located on the NMDA receptor complex was determined using the procedure of Kishimoto H. et al J. Neurochem 1981, 37, 1015–1024. The pKi with representative compounds of the invention are given in

| Example No. | pKi |
|---|---|
| 8 | 8.6 |
| 11 | 8.62 |
| 14 | 7.91 |
| 16 | 7.70 |
| 18 | 8.20 |
| 21 | 8.74 |
| 24 | 7.4 |
| 27 | 8.41 |
| 30 | 8.25 |
| 34 | 8.61 |
| 37 | 7.69 |
| 39 | 8.04 |
| 42 | 7.83 |
| 44 | 8.57 |
| 50 | 8.50 |
| 51 | 8.41 |
| 52 | 8.3 |

The ability of compounds of the invention to inhibit NMDA induced convulsions in the mouse was determined using the procedure of Chiamulera C et al. Psychpharmacology 1990, 102,–551–552. In this test the ability of the compound to inhibit the generalized seizures induced by an intracerebroventricular injection of NMDA in mice was examined. Thus the % inhibition of the NMDA induced convulsions when a compound of the invention was given the dose of 0.1 mg/kg I.V. was determined and representative results obtained for compounds of the invention are given in the following table.

| Ex No. | % Inhibition |
|---|---|
| 9 | 60 |
| 12 | 50 |
| 14 | 30 |
| 16 | 30 |
| 19 | 30 |
| 31 | 40 |
| 37 | 50 |
| 40 | 40 |
| 43 | 40 |
| 44 | 40 |

We claim:

1. A compound of formula (I)

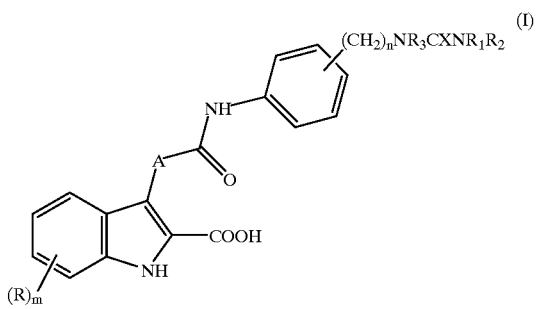

or a salt thereof wherein R represents a group selected from the group consisting of halogen, $C_{1-4}$ alkyl, $C_{1-4}$ alkoxy, amino, $C_{1-4}$ alkylamino, di-$C_{1-4}$ alkylamino, hydroxy, trifluoromethyl, trifluoromethoxy, nitro, cyano, $SO_2R_4$ or $COR_4$ wherein $R_4$ represents hydroxy, methoxy, amino, $C_{1-4}$ alkylamino or di $C_{14}$ alkylamino; m is zero or an integer 1 or 2;

A represents an ethynyl or an optionally substituted ethenyl group wherein the substituent may be one or two $C_{1-4}$ alkyl groups, an optionally substituted phenyl group substituted with up to three substituents selected from the group consisting of halogen, $C_{1-4}$ alkyl, $C_{1-4}$ alkoxy, amino, $C_{1-4}$ alkylamino, di-$C_{1-4}$ alkylamino, hydroxy, trifluoromethyl, carboxyl and methoxycarbonyl; including both cis and trans isomers;

$R_1$ represents hydrogen or an optionally substituted $C_{1-4}$ alkyl, or $C_{3-7}$ cycloalkyl which may be substituted or 1 or 2 $C_{1-4}$ alkyl groups, an optionally substituted phenyl group substituted with up to three substituents selected from the group consisting of halogen, $C_{1-4}$ alkyl, $C_{1-4}$ alkoxy, amino, $C_{1-4}$ alkylamino, di-$C_1$ alkylamino, hydroxy, trifluoromethyl, carboxyl and methoxycarbonyl; a 5 or 6 membered heteroaryl group in which the 5-membered heteroaryl group contains 1 or 2 heteroatoms selected from the group consisting of oxygen, sulphur and nitrogen, the 6-membered heteroaryl group contains 1 or 2 nitrogen atoms; an optionally substituted 5–7 membered saturated heterocyclic group containing one or two heteroatoms selected from the group consisting of oxygen, sulphur and nitrogen;

$R_2$ represents hydrogen or a $C_{1-4}$ alkyl group; or $R_1$ and $R_2$ together with the nitrogen atom to which they are attached represent a 5–7 membered heterocyclic ring which may contain an additional heteroatom selected from the group consisting of oxygen, sulphur and nitrogen;

$R_3$ represents hydrogen or $C_{1-4}$ alkyl;

n is zero or an integer from 1 to 4;

X is oxygen or sulphur.

2. A compound as claimed in claim 1 wherein m is 2 and R is chloro at the 4 and 6 position.

3. A compound as claimed in claim 1 wherein A is an unsubstituted ethenyl group in the trans configuration.

4. A compound as claimed in claim 1 wherein $R_3$ represents hydrogen.

5. A compound as claimed in claim 1 wherein $R_2$ represents hydrogen or methyl.

6. A compound as claimed in claim 1 wherein $R_1$ represents hydrogen, $C_{1-4}$ alkyl optionally substituted by carboxyl, $C_{3-6}$ cycloalkyl, phenyl optionally substituted by methoxy, 3-pyridyl, 4-tetrahydro-pyranyl.

7. A compound as claimed in claim 1 wherein $R_1$, $R_2$ and $R_3$ each represent hydrogen.

8. A compound as claimed in claim 1 wherein X represents oxygen.

9. A compound as claimed in claim 1 wherein n is 1 or 2.

10. 4,6-Dichloro-3-[(E)-2'-(4'-ureidomethyl phenylcarbamoyl)ethenyl]3-1H-indole 2-carboxylic acid and physiologically acceptable salts thereof.

11. A pharmaceutical composition comprising a compound as claimed in claim 1 in admixture with one or more physiologically acceptable carriers or excipients.

12. A method of treatment of a mammal of a disease selected from the group consisting of neurotoxic injury which follows cerebral stroke, thromboembolic stroke, hemorrhagic stroke, cerebral ischemia, cerebral vasospasm, hypoglycemia, hypoxia, anoxia, perinatal asphyxia cardiac arrest and epilepsy comprising administration of an effective amount of a compound as claimed in claim 1.

13. A compound as claimed in claim 1 wherein the substituent $(CH_2)_nNR_3C(X)NR_1R_2$ is at the 4-position on the phenyl ring.

14. A process for preparing compounds as defined in claim 1 which comprises:

(a) A process for preparing compounds of formula (I) in which A is an optionally substituted ethenyl group which comprises reacting a compound of formula (II) in which $R_1$, $R_3$, m and n have the meaning defined in formula (1), A is an optionally substituted ethenyl group, $R_5$ is carboxylic protecting group and $R_6$ represents hydrogen or a nitrogen protecting group

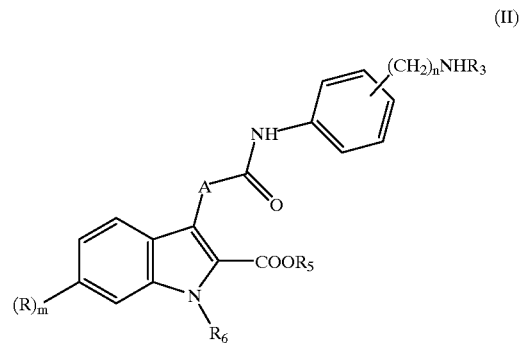

with the compounds of formula (III) wherein X represents oxygen or sulphur and $R_1$, $R_2$ have the meanings defined in formula (I) or is protected derivatives thereof, or the compounds (IV) wherein the $R_1$ and $R_2$ have the meaning defined in formula (I) or are protected derivatives thereof and $R_7$ is optionally substituted phenoxy, halogen, or imidazole group;

(b) A process for preparing compounds of formula (I), wherein R, m, $R_5$ and $R_6$ have the meanings defined above and A is optionally substituted ethenyl group which comprises reacting an activated derivative of the carboxylic acid (V)

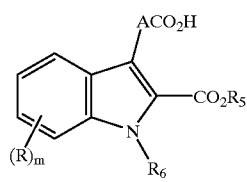

with the amine (VI)

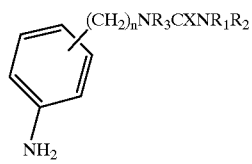

wherein $R_1$, $R_2$, $R_3$, n and X have the meanings defined in formula (I) or are protected derivative thereof;

(c) A process for preparing compounds of formula (I) wherein A is optionally substituted ethenyl group which comprises reacting a compound of formula (VII) in which R and m have the means given above, $R_5$ is a carboxyl protecting group, $R_6$ is hydrogen or a nitrogen protecting group and $R_8$ is hydrogen atom or a $C_{1-4}$ alkyl group,

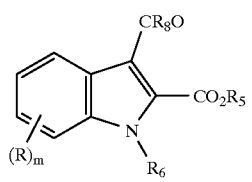

with an appropriate phosphorus reagent capable of converting the group $CR_8O$ into the group

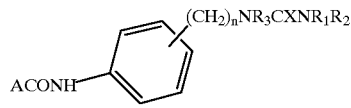

wherein n, X, $R_3$, $R_2$, $R_1$ have the meanings defined above for formula (I);

(d) A process for preparing compounds of formula (I) wherein A is an ethynyl group which comprises reacting compound (X) wherein $R_1$, $R_2$, $R_3$, m, n, and X have the meanings defined in formula (I) or are protected derivatives thereof, $R_1$ and $R_6$ have the meaning defined in formula (II) with the proviso that $R_6$ is not hydrogen and $R_{12}$ represents a halogen group

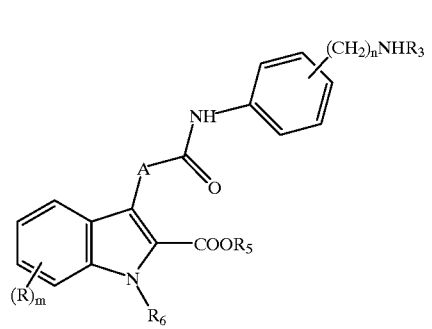

with a strong base lithium bis(trimethylsilyl)amide; and optionally, subjecting the resulting compound to one or more of the following operations;
  (i) removal of one or more protecting groups;
  (ii) isolation of the compound as a salt thereof;
  (iii) conversion of a compound of formula (I) into a physiologically acceptable salt thereof.

15. A compound of formula (II)

$$\text{(II)}$$

or a salt thereof wherein $R_1$, $R_3$ and m have the meanings defined in claim 1, A is an optionally substituted ethenyl group wherein the substituent may be one or two $C_{1-4}$ alkyl groups, an optionally substituted phenyl group substituted with up to three substituents selected from the group consisting of halogen, $C_{1-4}$ alkyl, $C_{1-4}$ alkoxy, amino, $C_{1-4}$ alkylamino, di-$C_{1-4}$ alkylamino, hydroxy, trifluoro-methyl,carboxyl and methoxycarbonyl; including both cis and trans isomers; n is 1 to 4, $R_5$ is hydrogen or a carboxyl protecting group and $R_6$ is hydrogen or a nitrogen protecting group.

16. A compound as claimed in claim 1 wherein $R_1$ is furanyl, thiophenyl, imidazolyl, isoxazolyl, thiazolyl, oxazolyl, pyridyl or pyrimidinyl.

17. A compound as claimed in claim 1 wherein $R_1$ is 4-tetrahydropyranyl, pyrrolidinyl, piperidinyl, pyrrolidinyl, pyrrolidino, morpholino, thiomophlino or piperazino.

18. A compound as claimed in claim 1 wherein $R_1$ and $R_2$ together with the nitrogen atom to which they are attached form a group selected from the group consisting of morpholino, 2,6-dimethylmorpholino, piperidino, pyrrolidino, piperazino, N-methylpiperazino, N-imidazoline or N-imidazole.

* * * * *